(12) United States Patent
Fiegen et al.

(10) Patent No.: US 8,604,049 B2
(45) Date of Patent: Dec. 10, 2013

(54) 4-DIMETHYLAMINO-PHENYL-SUBSTITUTED NAPHTHYRIDINES, AND USE THEREOF AS MEDICAMENTS

(75) Inventors: Dennis Fiegen, Biberach (DE); Sandra Handschuh, Biberach (DE); Silke Hobbie, Biberach (DE); Matthias Hoffmann, Mittelbiberach (DE); Takeshi Kono, Osaka (JP); Yayoi Sato, Hyogo (JP); Andreas Schnapp, Biberach (DE); Annette Schuler-Metz, Ulm (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 276 days.

(21) Appl. No.: 13/057,330

(22) PCT Filed: Jul. 23, 2009

(86) PCT No.: PCT/EP2009/059493
§ 371 (c)(1),
(2), (4) Date: Apr. 5, 2011

(87) PCT Pub. No.: WO2010/015518
PCT Pub. Date: Feb. 11, 2010

(65) Prior Publication Data
US 2011/0263549 A1   Oct. 27, 2011

(30) Foreign Application Priority Data
Aug. 5, 2008 (EP) .................................... 08161843

(51) Int. Cl.
| | |
|---|---|
| A61K 31/573 | (2006.01) |
| A61K 31/4375 | (2006.01) |
| A61P 11/00 | (2006.01) |
| A61P 19/10 | (2006.01) |
| A61P 1/04 | (2006.01) |
| A61P 31/14 | (2006.01) |
| A61P 7/06 | (2006.01) |
| A61P 25/00 | (2006.01) |
| A61P 19/02 | (2006.01) |
| C07D 471/04 | (2006.01) |

(52) U.S. Cl.
USPC ........................... 514/300; 514/171; 546/122

(58) Field of Classification Search
USPC ................... 514/300, 171; 546/122
See application file for complete search history.

(56) References Cited

U.S. PATENT DOCUMENTS

| 7,321,041 B2* | 1/2008 | Cywin et al. .................. 546/122 |
| 2003/0158195 A1 | 8/2003 | Cywin et al. |
| 2008/0188467 A1 | 8/2008 | Wong et al. |
| 2011/0263549 A1 | 10/2011 | Fiegen et al. |
| 2012/0028939 A1 | 2/2012 | Hoffmann et al. |

FOREIGN PATENT DOCUMENTS

| EP | 1396488 A1 | 3/2004 |
| WO | 03057695 A1 | 7/2003 |
| WO | 2003057695 | * 7/2003 |
| WO | 2008133753 A2 | 11/2008 |
| WO | 2010015518 A2 | 2/2010 |
| WO | 2010015520 A1 | 2/2010 |
| WO | 2011092128 A1 | 8/2011 |

OTHER PUBLICATIONS

Weinblatt et al., Arthritis & Rheumatism, vol. 58, No. 11. (2008), pp. 3309-3318.*

(Continued)

*Primary Examiner* — Niloofar Rahmani
(74) *Attorney, Agent, or Firm* — Michael P. Morris; Usha R. Patel

(57) ABSTRACT

The invention relates to novel substituted naphthyridines of formula 1 as well as pharmacologically acceptable salts, diastereomers, enantiomers, racemates, hydrates, or solvates thereof. In formula 1, $R^1$ can represent a group A selected from among the group comprising —O—$R^3$, —N$R^3R^4$, —C$R^3R^4R^5$, -(ethyne)-$R^3$, —S—$R^3$, —SO—$R^3$, and $SO_2$—$R^3$, or $R^1$ represents a group B selected from among the group comprising: —$C_{6-10}$-aryl; —a five-membered to ten-membered, monocyclic or bicyclic heteroaryl containing 1 to 3 heteroatoms independently selected from among the group comprising N, O, and S, wherein said heteroaryl is linked to the structure according to formula 1 via a C atom or an N atom; —a three-membered to ten-membered, monocyclic or bicyclic, saturated or partially saturated heterocycle containing 1 to 3 heteroatoms independently selected from among the group comprising N, O, and S, wherein said heterocycle is linked to the structure according to formula 1 via a C atom or an N atom; and —a 5-membered to 11-membered spiro group which can optionally contain 1, 2, or 3 heteroatoms independently selected from among the group comprising N, O, and S, wherein said spiro group is linked to the structure according to formula 1 via a C atom or an N atom, wherein said group B can be optionally substituted as described in claims 1, and $R^3$, $R^4$, $R^5$, $R^6$, and m can have the meanings indicated in claim 1. The invention also relates to pharmaceutical compositions containing said compounds.

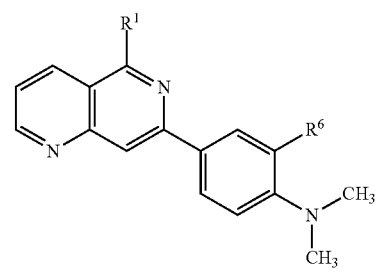

9 Claims, No Drawings

(56) References Cited

OTHER PUBLICATIONS

Xie et al., Bioorganic & Medicinal Chemistry Letters (2009), 19(7), 1944-1949.*
Cywin et al., Bioorganic & Medicinal Chemistry Letters (2003), 13(8), 1415-1418.*
International Search Report and Written Opinion for PCT/EP2009/059493 mailed May 19, 2010.
Cywin, C.L. et al., "Discovery and SAR of Novel [1,6]Naphthyridines as Potent Inhibitors of Spleen Tyrosine Kinase (SYK)". Bioorganice & Medicinal Chemistry Letters, 13, 2003, 1415-1418.
Brun, E.M. et al., "New approach to condensed pyrid-2-ones". ARKIVOC (Gainesville, FL, U.S.) [online computer file], coden: AGFUAR URL: http://www.arkat-usa.org/ark/journal/2002/Part(x)_general/2-615c/615c.pdf, vol. 2002, No. (x), Jan. 22, 2003, pp. 80-89.
Ames, D.E., "Condensation of beta-Dicarbonyl Compounds with Halogenopyridinecarboxylic Acids. A Convenient sythesis of Some Naphthridine Derivatives". Journal of the Chemical Society, Perkin Transactions 1, Chemical Society, Letchworth; GB LNKD-DOI:10.1029/P19720000705, Jan. 1, 1972, pp. 705-710.
International Search Report of corresponding PCT Appln No. PCT/EP2009/059493 dated Sep. 21, 2009.

\* cited by examiner

4-DIMETHYLAMINO-PHENYL-SUBSTITUTED NAPHTHYRIDINES, AND USE THEREOF AS MEDICAMENTS

The invention relates to new substituted naphthyridines of formula 1, as well as pharmacologically acceptable salts, diastereomers, enantiomers, racemates, hydrates or solvates thereof,

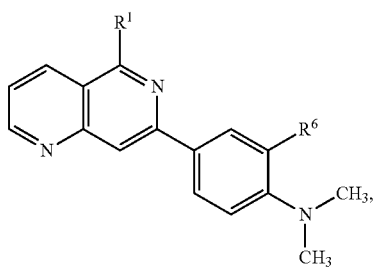

wherein
$R^1$ denotes a group A selected from among —O—$R^3$, —$NR^3R^4$, —$CR^3R^4R^5$, -(ethyne)-$R^3$, —S—$R^3$, —SO—$R^3$ and $SO_2$—$R^3$
or
$R^1$ denotes a group B selected from among
$C_{6-10}$-aryl,
five- to ten-membered, mono- or bicyclic heteroaryl with 1-3 heteroatoms selected independently of one another from among N, O and S; wherein this heteroaryl is linked to the structure according to formula 1 via either a C atom or an N atom,
three- to ten-membered, mono- or bicyclic, saturated or partly saturated heterocyclic group with 1-3 heteroatoms selected independently of one another from among N, O and S, while this heterocyclic group is linked to the structure according to formula 1 via either a C atom or an N atom,
and
5- to 11-membered spiro group which may optionally contain 1, 2 or 3 heteroatoms selected independently of one another from among N, O and S, where this spiro group is linked to the structure according to formula 1 via either a C atom or an N atom,
where this group B may optionally be substituted as described in claim 1 and $R^3$, $R^4$, $R^5$, $R^6$ and m may have the meanings given in claim 1, as well as medicaments that contain these compounds.

1. BACKGROUND TO THE INVENTION

1.1 SYK-Inhibitors

The present invention describes new substituted naphthyridines that inhibit the protein kinase Syk (spleen tyrosine kinase), the preparation and formulation thereof and their use for preparing a medicament.

Syk is an intracellular tyrosine kinase that has an important mediator function in the signal transduction of different receptors in B-cells, mast cells, monocytes, macrophages, neutrophils, T-cells, dendritic cells and epithelial cells. The receptors in which Syk performs an important function in signal transduction include for example the receptors for IgE (FcεRI) and IgG (FcγR1) on mast cells and B cells, the B-cell receptor (BCR) and the T-cell receptor (TCR) on B- and T-cells, the ICAM1 receptor (ICAM1R) on epithelial cells of the respiratory tract, the DAP12-receptor on natural killer cells, dendritic cells and osteoclasts, the dectin 1-receptor on a subpopulation of T-helper cells (Th-17 cells), as well as the integrin receptors for β1-, β2- and β3-integrins on neutrophils, monocytes and macrophages (Wong et al.; Expert Opin. Investig. Drugs (2004) 13(7), 743-762; Ulanova et al.; Expert Opion. Ther. Target (2005) 9(5); 901-921; Wang et al.; J. Immunol. (2006) 177, 6859-6870; LeibundGut-Landmann et al.; Nature Immunology (2007) 8, 630-638; Slack et al., European J. Immunol. (2007) 37, 1600-1612). The best description is of the molecular processes during the signal transduction of the FcεRI. In mast cells the binding of IgE to FcεRI causes the cross-linking of IgE-receptors and the recruiting and activation of Lyn (a tyrosine kinase from the Src family). Active Lyn phoshorylates so-called ITAM motifs, which are present in may of the receptors listed above, and thereby generates binding sites for the SH2-domain of Syk. As a result of the binding to the ITAM motif Syk is activated and then phosphorylates various substrates which are needed for the release of allergic and inflammatory mediators such as e.g. histamine and β-hexosamidase (βHA), as well as for the synthesis of lipid mediators, such as e.g. prostaglandins and leukotrienes.

In view of its central function in different signal transduction pathways Syk has been discussed as a therapeutic target for different diseases such as e.g. Allergic rhinitis, asthma, autoimmune diseases, rheumatoid arthritis, osteopenia, osteoporosis, COPD and various leukaemias and lymphomas (Wong et al.; Expert Opin. Investig. Drugs (2004) 13(7), 743-762; Ulanova et al.; Expert Opion. Ther. Target (2005) 9(5); 901-921; Sigh and Masuda. Annual Reports in Medicinal Chemistry (2007) Vol 42; 379-391; Bajpai et al.; Expert Opin. Investig. Drugs (2008) Vol 15 (5); 641-659; Masuda and Schmitz; PPT (2008) Vol 21; 461-467).

Allergic rhinitis and asthma are diseases associated with allergic reactions and inflammatory processes and involving different cell types such as e.g. Mast cells, eosinophils, T-cells and dendritic cells. After exposure to allergens has occurred, the high affinity immunoglobulin receptors for IgE (FcεRI) and IgG (FcγR1) are activated and induce the release of pro-inflammatory mediators and bronchoconstrictors. An inhibitor of the Syk kinase activity should thus be able to inhibit these steps.

Rheumatoid arthritis (RA) is an autoimmune disease in which the bones and ligaments structures surrounding the joints are progressively destroyed. In the pathophysiology of RA, B-cells play a significant role, as has been demonstrated for example by the therapeutic use of rituximab, a B cell-depleting antibody. In addition to the function of Syk in the signal transduction of the BCR (which after being stimulated also induces the release of pro-inflammatory mediators), Syk also plays an important part in the maturation and proliferation of B cells (Cheng et al. Nature (1995) 378, 303-306, Cornall et al., PNAS (2000) 97(4), 1713-1718). An inhibitor of the Syk kinase activity might thus offer a therapeutic option for the treatment of autoimmune diseases such as RA and diseases with an increased proliferation of B cells, such as e.g. B-cell lymphocytes.

Chronic obstructive pulmonary disease (COPD) is characterised by a successive deterioration in lung function and chronic inflammation of the airways, which is initiated and produced by noxious substances of all kinds and contributes to the maintenance of the course of the disease. At a cellular level, in COPD there is in particular a multiplication of T-lymphocytes, neutrophils, granulocytes and macrophages. In particular, there is an increase in the number of CD8-positive lymphocytes, that is directly connected with the impairment of lung function. Another characteristic of COPD are acute deteriorations in lung function (exacerbations), characterised by viral (e.g. Rhinovirus), or bacterial (e.g. *Streptococcus pneumoniae, Haemophilus influenzae* and *Moraxella catarrhalis*) infections.

In view of the pro-inflammatory function of Syk in macrophages, T-cells and neutrophils as described above (see: Wong et al.; Expert Opin. Investig. Drugs (2004) 13(7), 743-762; and references cited therein) an inhibitor of the Syk kinase activity could be a new therapeutic approach to the treatment of the inflammatory processes that underlie COPD. It has also been shown that Syk in epithelial cells of the respiratory tract is involved in the ICAM1R-mediated uptake and subsequent replication of the Rhinovirus and that a siRNA against Syk blocks these steps (Wang et al.; J. Immunol. (2006) 177, 6859-6870; Lau et al.; J. Immunol. (2008) 180, 870-880). Thus, an inhibitor of the Syk kinase activity could also be used therapeutically in exacerbations caused by Rhinoviruses.

Various studies suggest that Syk is involved in the malignant transformation of lymphocytes (summarised in Sigh and Masuda. Annual Reports in Medicinal Chemistry (2007) Vol 42; 379-391). A TEL-Syk fusion protein with a constitutive Syk activity transformed B cells of a patient with myelodysplastic syndrome, a constitutively active ITK-Syk fusion protein was isolated from patients with T-cell lymphomas. Moreover, constitutively active Syk was found in B-cell lymphoma cells of patients. On the basis of these data it seems that Syk is a proto-oncogene in haematopoietic cells and represents a potential target for the treatment of certain leukaemias and lymphomas.

1.2 Prior Art

BE 835770 describes 5-amino-1,6-naphthyridine with an antimicrobial activity. U.S. Pat. No. 3,928,367, U.S. Pat. No. 4,017,500, U.S. Pat. No. 4,115,395 and U.S. Pat. No. 4,260,759 describe 5-amino-1,6-naphthyridines with an antifungal and antibacterial activity. WO 9918077 describes 5-piperazinyl-1,6-naphthyridines as serotonin antagonists. U.S. Pat. No. 7,321,041 describes substituted [1,6]-naphthyridines as SYK-inhibitors, although they have a completely different substitution pattern from the compounds according to the invention.

2. DESCRIPTION OF THE INVENTION

Surprisingly it has now been found that naphthyridines of formula 1 are particularly suitable for the treatment of respiratory complaints, allergic diseases, osteoporosis, gastrointestinal diseases, autoimmune diseases, inflammatory diseases and diseases of the peripheral or central nervous system, particularly for the treatment of asthma, allergic rhinitis, rheumatoid arthritis, allergic dermatitis and COPD.

The present invention therefore relates to compounds of formula 1,

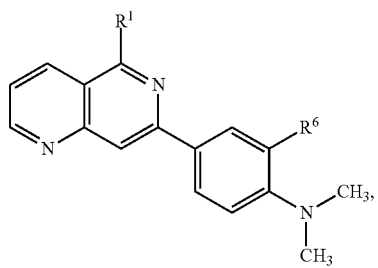

1 wherein
$R^1$ is a group A selected from among —O—$R^3$, —N$R^3R^4$, —C$R^3R^4R^5$, -(ethyne)-$R^3$, —S—$R^3$, —SO—$R^3$ and SO$_2$—$R^3$ or
$R^1$ is a group B selected from among
$C_{6-10}$-aryl,
five- to ten-membered, mono- or bicyclic heteroaryl with 1-3 heteroatoms selected independently of one another from among N, O and S; while this heteroaryl is linked to the structure according to formula 1 via either a C atom or an N atom,
three- to ten-membered, mono- or bicyclic, saturated or partially saturated heterocyclic group with 1-3 heteroatoms selected independently of one another from among N, O and S, while this heterocyclic group is linked to the structure according to formula 1 via either a C atom or an N atom,
and
5- to 11-membered spiro group which may optionally contain 1, 2 or 3 heteroatoms selected independently of one another from among N, O and S, while this spiro group is linked to the structure according to formula 1 via either a C atom or an N atom,
wherein this group B may optionally be substituted by one or more groups selected independently of one another from among H, halogen, —$C_{1-3}$-alkyl, —NH($C_{1-4}$-alkyl), —N($C_{1-4}$-alkyl)$_2$, —NH$_2$, —$C_{1-3}$-alkyl-OH, —OH, oxo, —CO—NH$_2$, —$C_{1-3}$-alkylene-CO—NH$_2$, —CO—NH—($C_{1-3}$-alkyl), —$C_{1-3}$-alkylene-CO—NH($C_{1-3}$-alkyl), —CO—NH($C_{3-5}$-cycloalkyl), —$C_{1-3}$-alkylene-CO—NH($C_{3-5}$-cycloalkyl), —NH—CO—NH$_2$, —NH—CO—NH($C_{1-3}$-alkyl), —NH—CO—N($C_{1-3}$-alkyl)$_2$, O—$C_{1-3}$-alkyl, —($C_{1-3}$-alkylene)-NH$_2$, -phenyl and —CO—($C_{1-5}$-alkyl),
$R^3$ is H
or a group selected from among —$C_{1-6}$-alkyl, —$C_{1-6}$-fluoroalkyl, —($C_{1-5}$-alkyl)-OH, —$C_{6-10}$-aryl, —($C_{1-4}$-alkylene)-($C_{6-10}$-aryl), -ethenyl, —($C_{1-4}$-alkylene)-(ethen), -ethynyl, —($C_{1-4}$-alkylene)-(ethyne), —($C_{1-4}$-alkylene)-(ethyne)-NH$_2$, —($C_{1-4}$-alkylene)-(ethyne)-($C_{1-4}$-alkylene)-NH$_2$, —NH($C_{1-3}$-alkyl), —($C_{1-4}$-alkylene)-NH($C_{1-3}$-alkyl), —CHOH—($C_{1-4}$-alkylene)-NH$_2$, —($C_{1-4}$-alkylene)-CHOH—($C_{1-4}$-alkylene)-NH$_2$, —($C_{1-4}$-alkylene)-CHOH—NH$_2$, —CHOH—NH$_2$, mono- or bicyclic, saturated or partly saturated —$C_{3-10}$-cycloalkyl, mono- or bicyclic, saturated or partly saturated —($C_{1-4}$-alkylene)-$C_{3-10}$-cycloalkyl, -(Het), —($C_{1-4}$-alkylene)-(Het), -(Hetaryl), and —($C_{1-4}$-alkylene)-(Hetaryl),
while this group
may optionally be substituted by one or more groups selected independently of one another from among H, —OH, -oxo, —COON, -halogen, —$C_{1-3}$-alkyl, —$C_{1-3}$-haloalkyl, —$C_{1-3}$-alkyl-OH, —$C_{3-7}$-cycloalkyl, —O—($C_{1-4}$-alkyl), —NH($C_{1-4}$-alkyl), —($C_{1-4}$-alkylene)-NH($C_{1-4}$-alkyl), —N($C_{1-4}$-alkyl)$_2$, —($C_{1-4}$-alkylene)-N($C_{1-4}$-alkyl)$_2$, —NH—CO—NH$_2$, —($C_{1-4}$-alkylene)-NH—CO—NH$_2$, —CO—NH$_2$, —($C_{1-4}$-alkylene)-CO—NH$_2$, —CO—NH($C_{1-3}$-alkyl), —($C_{1-4}$-alkylene)-CO—NH($C_{1-3}$-alkyl), —CO—N($C_{1-3}$-alkyl)$_2$, —($C_{1-4}$-alkylene)-CO—N($C_{1-3}$-alkyl)$_2$, —NH—(CO)$_m$—NH$_2$, —NH—($C_{1-4}$-alkylene)-(CO)$_m$—NH$_2$, —NH—(CO)$_m$—NH($C_{1-3}$-alkyl), —NH—($C_{1-4}$-alkylene)-(CO)$_m$—NH($C_{1-3}$-alkyl), —NH—(CO)$_m$—N($C_{1-3}$-alkyl)$_2$, —NH—($C_{1-4}$-alkylene)-(CO)$_m$—N($C_{1-3}$-alkyl)$_2$, —O—($C_{2-4}$-alkylene)-NH$_2$, —O—($C_{2-4}$-alkylene)-NH($C_{1-3}$-alkyl), —O—($C_{2-4}$-alkylene)-N($C_{1-3}$-alkyl)$_2$, —NH—CO—($C_{1-3}$-alkyl), —($C_{1-4}$-alkylene)-NH—CO—($C_{1-3}$-alkyl), $C_{3-5}$-cycloalkyl, —SO$_2$—($C_{1-4}$-alkyl), —SO$_2$—($C_{3-5}$-cycloalkyl), —SO$_2$—NH$_2$, —SO$_2$—NH—$C_{1-3}$-alkyl, —SO$_2$—N($C_{1-3}$-alkyl)$_2$, —SO$_2$-(Het), —O-(Het), —O—($C_{1-4}$-alkylene)-(Het), —NH-(Het), —NH—

($C_{1-4}$-alkylene)-(Het), —NH-(Hetaryl), —NH—($C_{1-4}$-alkylene)-(Hetaryl), -(Het) and —($C_{1-4}$-alkylene)-(Het), while (Het) represents a three- to ten-membered, saturated or partly saturated, mono- or bicyclic heterocyclic group, optionally substituted by 1-3 groups selected from $C_{1-3}$-alkyl, halogen, $CH_2$—$NH_2$, $NH_2$, OH, CO—$NH_2$ and oxo, which contains 1, 2 or 3 heteroatoms selected independently of one another from among N, O and S, and (Hetaryl) denotes a five- to ten-membered, mono- or bicyclic heteroaryl, optionally substituted by 1, 2 or 3 groups selected from $C_{1-3}$-alkyl, halogen, $CH_2$—$NH_2$, $NH_2$, OH, CO—$NH_2$ and oxo, which contains 1-3 heteroatoms selected independently of one another from among N, O and S, wherein m=0 or 1 and $R^4$ and $R^5$ denote H, methyl or ethyl and $R^6$ denotes methyl, ethyl, propyl, —O-methyl, —O-ethyl, —O-propyl, Br, Cl, F or phenyl, as well as pharmaceutically acceptable salts, diastereomers, enantiomers, racemates, hydrates and solvates thereof.

A preferred object of the present invention relates to compounds of the above formula 1 with the above-mentioned definitions of the individual variables, wherein $R^6$ is methyl, and pharmaceutically acceptable salts, diastereomers, enantiomers, racemates, hydrates and solvates thereof.

Also preferred are compounds of formula 1 with the above-mentioned definitions of the individual variables, wherein $R^1$ is —O—$R^3$ or —$NR^3R^4$, and pharmaceutically acceptable salts, diastereomers, enantiomers, racemates, hydrates and solvates thereof.

The present invention preferably further relates to compounds of formula 1 with the above-mentioned definitions of the individual variables, wherein $R^1$ is —O—$R^3$ or —$NR^3R^4$ and wherein (Het) denotes a three- to seven-membered, saturated or partly saturated, monocyclic heterocyclic group, optionally substituted by 1-3 groups selected from methyl, ethyl propyl, isopropyl, F, Cl, Br, $CH_2$—$NH_2$, $NH_2$, OH, CO—$NH_2$ and oxo, which contains 1, 2 or 3 heteroatoms selected independently of one another from among N, O and S, and wherein (Hetaryl) denotes a five- to six-membered, monocyclic heteroaryl, optionally substituted by 1, 2 or 3 groups selected from methyl, ethyl propyl, isopropyl, F, Cl, Br, $CH_2$—$NH_2$, $NH_2$, OH, CO—$NH_2$ and oxo, which contains 1-3 heteroatoms selected independently of one another from among N, O and S, as well as pharmaceutically acceptable salts, diastereomers, enantiomers, racemates, hydrates and solvates thereof.

In another preferred aspect the present invention relates to compounds of formula 1 with the above-mentioned definitions of the individual variables, wherein $R^1$ is selected from among five- to ten-membered, mono- or bicyclic heteroaryl with 1-3 heteroatoms selected independently of one another from among N, O and S; where at least one of the 1-3 heteroatoms is an N atom and three- to ten-membered, mono- or bicyclic, saturated or partly saturated heterocyclic group with 1-3 heteroatoms selected independently of one another from among N, O and S, where at least one of the 1-3 heteroatoms is an N atom, while the above-mentioned heteroaryls and heterocycles are each linked to the structure according to formula 1 by means of the at least one N atom, or wherein $R^1$ is a 5- to 11-membered spiro group, which contains 1, 2 or 3 heteroatoms selected independently of one another from among N, O and S, wherein at least one of the 1-3 heteroatoms of this spiro group is an N atom and wherein the spiro group is linked to the structure according to formula 1 via this N atom, as well as pharmaceutically acceptable salts, diastereomers, enantiomers, racemates, hydrates and solvates thereof.

In particular the present invention relates to compounds of formula 1 with the above-mentioned definitions of the individual variables, where $R^1$ is selected from among

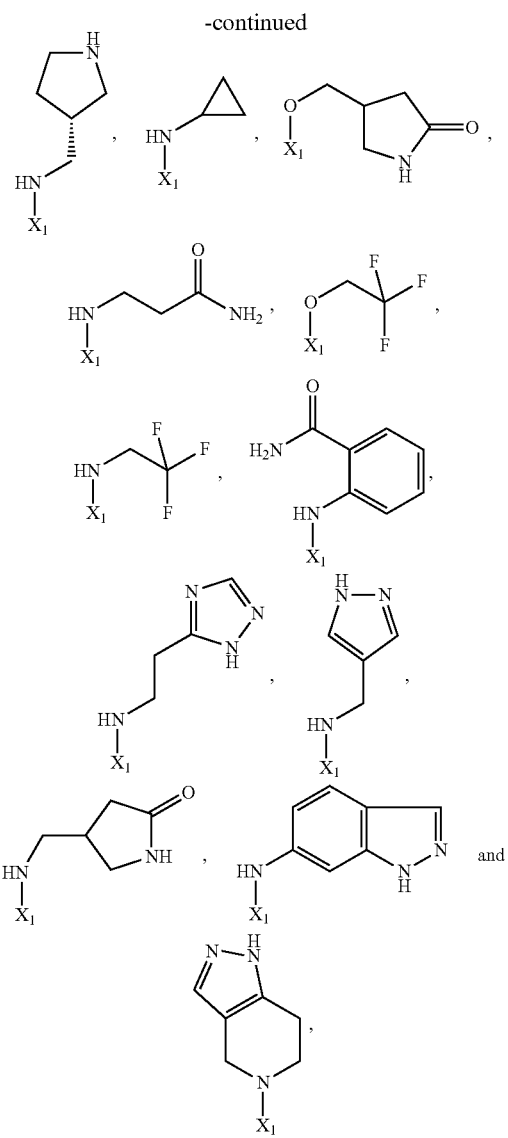

$X_1$ denotes the point of attachment of $R^1$ to the structure of formula 1 and wherein $R^6$ is methyl, as well as pharmaceutically acceptable salts, diastereomers, enantiomers, racemates, hydrates and solvates thereof.

The invention further relates to the above compounds of formula 1 with the above-mentioned definitions of the individual variables as pharmaceutical compositions.

The invention further relates to the use of the above compounds of formula 1 with the above-mentioned definitions of the individual variables for preparing a medicament for the treatment of diseases treated by inhibiting the SYK enzyme.

In another preferred aspect the invention relates to the use of the above compounds of formula 1 with the above-mentioned definitions of the individual variables for preparing a medicament for the treatment of diseases selected from among allergic rhinitis, asthma, COPD, adult respiratory distress syndrome, bronchitis, dermatitis and contact dermatitis, allergic dermatitis, allergic rhinoconjunctivitis, rheumatoid arthritis, anti-phospholipid syndrome, Berger's disease, Evans's syndrome, ulcerative colitis, allergic antibody-based glomerulonephritis, granulocytopenia, Goodpasture's syndrome, hepatitis, Henoch-Schönlein purpura, hypersensitivity vasculitis, immunohaemolytic anaemia, idiopathic thrombocytopenic purpura, Kawasaki syndrome, allergic conjunctivitis, lupus erythematodes, neutropenia, non-familial lateral sclerosis, Crohn's disease, multiple sclerosis, myasthenia gravis, osteoporosis, osteolytic diseases, osteopenia, psoriasis, Sjögren's syndrome, sclerodermy, urticaria/angiooedema, Wegener's granulomatosis and coeliac disease.

In a particularly preferred aspect the present invention relates to the use of the above compounds of formula 1 with the above-mentioned definitions of the individual variables for preparing a medicament for the treatment of diseases selected from among asthma, COPD, allergic rhinitis, adult respiratory distress syndrome, bronchitis, allergic dermatitis, contact dermatitis, idiopathic thrombocytopenic purpura, rheumatoid arthritis and allergic rhinoconjunctivitis.

The present invention relates in particular to the use of the above compounds of formula 1 with the above-mentioned definitions of the individual variables for preparing a medicament for the treatment of diseases selected from among asthma, COPD, allergic rhinitis, allergic dermatitis and rheumatoid arthritis.

Moreover the present invention preferably relates to pharmaceutical formulations which contain one or more compounds of formula 1 with the above-mentioned definitions of the individual variables.

The invention further relates to pharmaceutical formulations which contain one or more compounds of formula 1 with the above-mentioned definitions of the individual variables, in combination with an active substance selected from among the betamimetics, corticosteroids, PDE4-inhibitors, EGFR-inhibitors and LTD4-antagonists, CCR3-inhibitors, iNOS-inhibitors and other SYK-inhibitors.

In another preferred aspect the invention relates to the following intermediate products in the preparation of the above compounds according to formula 1 selected from among

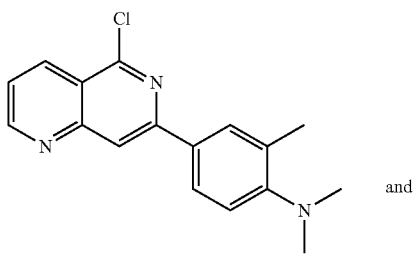

6.1

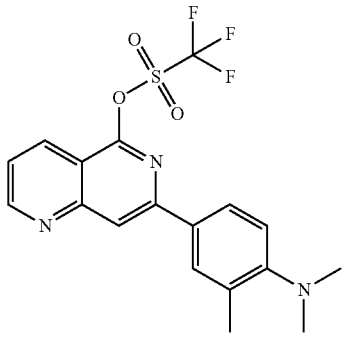

6.2

3. TERMS AND DEFINITIONS USED

Unless stated otherwise, all the substituents are independent of one another. If for example a number of $C_{1-6}$-alkyl groups are possible substituents at a group, in the case of three substituents, for example, $C_{1-6}$-alkyl could represent, independently of one another, a methyl, an n-propyl and a tert-butyl.

Within the scope of this application, in the definition of possible substituents, these may also be presented in the form of a structural formula. An asterisk (*) in the structural formula of the substituent is to be understood as being the linking point to the rest of the molecule. Moreover, the atom of the substituent following the linking point is understood as being the atom in position number 1. Thus for example the groups N-piperidinyl (I), 4-piperidinyl (II), 2-tolyl (III), 3-tolyl (IV) and 4-tolyl (V) are represented as follows:

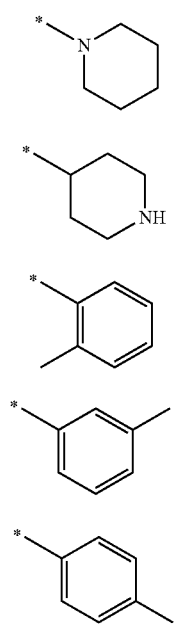

If there is no asterisk (*) in the structural formula of the substituent, each hydrogen atom may be removed at the substituent and the valency thus freed may serve as a binding site to the rest of a molecule. Thus, for example, VI

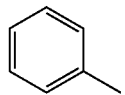

may represent 2-tolyl, 3-tolyl, 4-tolyl and benzyl.

Alternatively to the * within the scope of this application $X_1$ is also understood as being the linking point of the group $R^1$ to the structure of formula 1 and $X_2$ as being the linking point of the group $R^2$ to the structure of formula 1.

By the term "$C_{1-6}$-alkyl" (including those which are part of other groups) are meant branched and unbranched alkyl groups with 1 to 6 carbon atoms and by the term "$C_{1-3}$-alkyl" are meant branched and unbranched alkyl groups with 1 to 3 carbon atoms. "$C_{1-4}$-alkyl" accordingly denotes branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc., may also optionally be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples of these include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl includes also 1-methylethylene and butylene includes 1-methylpropylene, 1,1-dimethylethylene, 1,2-dimethylethylene.

If the carbon chain is substituted by a group which together with one or two carbon atoms of the alkylene chain forms a carbocyclic ring with 3, 5 or 6 carbon atoms, this includes, inter alia, the following examples of the rings:

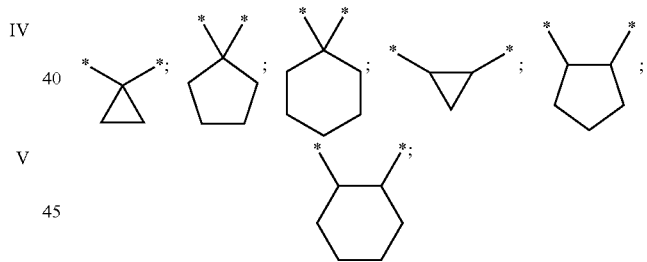

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples of these include:

ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1, 2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

By the term "aryl" (including those which are part of other groups) are meant aromatic ring systems with 6 or 10 carbon atoms. Examples include: phenyl or naphthyl, the preferred aryl group being phenyl. Unless stated otherwise, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include: benzyl, 1- or 2-phenylethyl or 1- or 2-naphthylethyl. Unless stated otherwise, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—even though they are already included under "aryl-$C_{1-6}$-alkylene"—branched and unbranched alkylene groups with 1 to 6 carbon atoms, which are substituted by a heteroaryl.

A heteroaryl of this kind includes five- or six-membered heterocyclic aromatic groups or 5-10-membered, bicyclic heteroaryl rings which may contain one, two, three or four heteroatoms selected from among oxygen, sulphur and nitrogen, and contain so many conjugated double bonds that an aromatic system is formed. The following are examples of five- or six-membered heterocyclic aromatic groups or bicyclic heteroaryl rings:

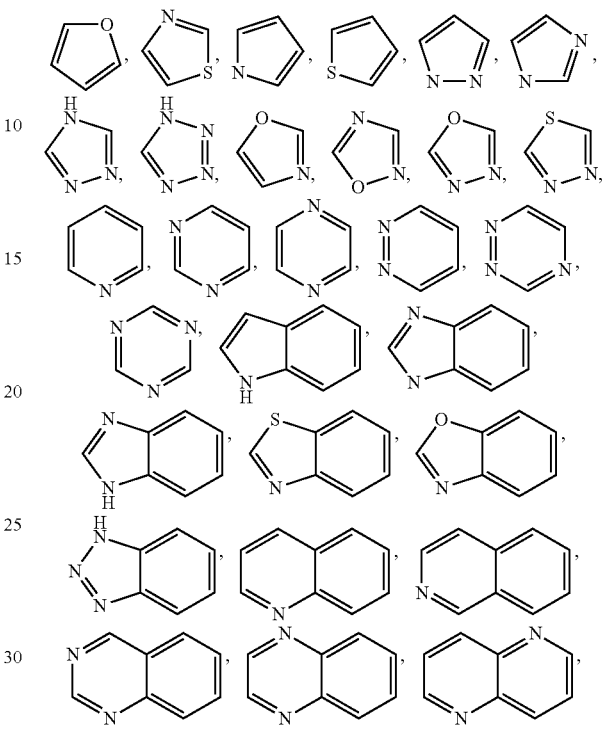

Unless otherwise stated, these heteroaryls may be substituted by one or more groups selected from among methyl, ethyl, iso-propyl, tert-butyl, hydroxy, fluorine, chlorine, bromine and iodine.

The following are examples of heteroaryl-$C_{1-6}$-alkylenes:

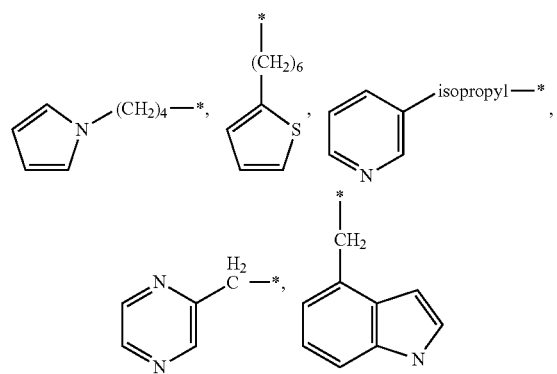

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{3-10}$-cycloalkyl" are also meant monocyclic alkyl groups with 3 to 7 carbon atoms and also bicyclic alkyl groups with 7 to 10 carbon atoms, or monocyclic alkyl groups which are bridged by at least one $C_{1-3}$-carbon bridge.

By the term "heterocyclic rings" or "heterocycle" are meant, unless stated otherwise, five-, six- or seven-membered, saturated, partially saturated or unsaturated heterocyclic rings which may contain one, two or three heteroatoms, selected from among oxygen, sulphur and nitrogen, while the ring may be linked to the molecule through a carbon atom or through a nitrogen atom, if there is one. Although included by the term "heterocyclic rings" or "heterocycles", the term "saturated heterocyclic ring" refers to five-, six- or seven-membered saturated rings. Examples include:

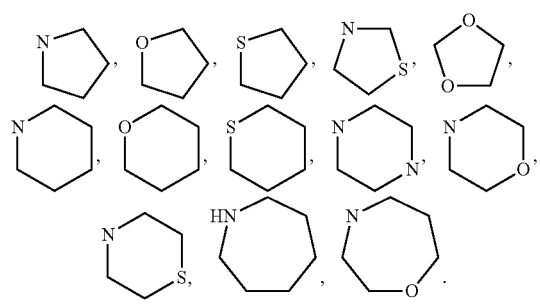

Although included by the term "heterocyclic rings" or "heterocyclic group", the term "partially saturated heterocyclic group" refers to five-, six- or seven-membered partially saturated rings which contain one or two double bonds, without so many double bonds being produced that an aromatic system is formed. Examples include:

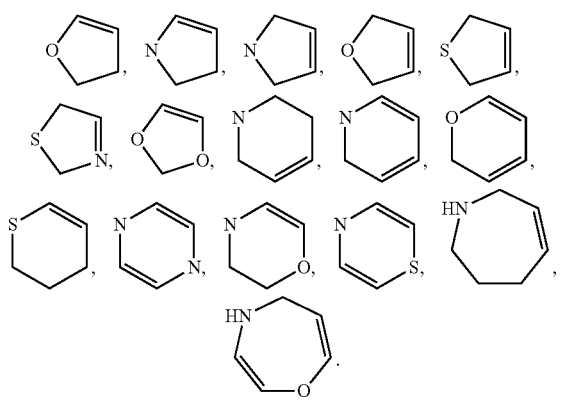

Although included by the term "heterocyclic rings" or "heterocycles", the term "heterocyclic aromatic rings", "unsaturated heterocyclic group" or "heteroaryl" refers to five- or six-membered heterocyclic aromatic groups or 5-10-membered, bicyclic heteroaryl rings which may contain one, two, three or four heteroatoms, selected from among oxygen, sulphur and nitrogen, and contain so many conjugated double bonds that an aromatic system is formed. Examples of five- or six-membered heterocyclic aromatic groups include:

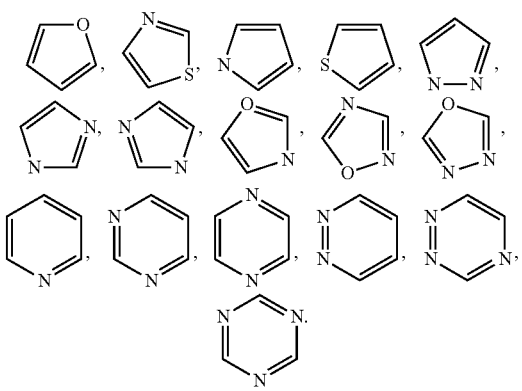

Unless otherwise mentioned, a heterocyclic ring (or heterocycle) may be provided with a keto group. Examples include:

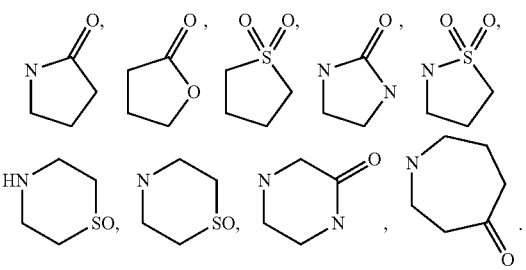

Although covered by the term "cycloalkyl", the term "bicyclic cycloalkyls" generally denotes eight-, nine- or ten-membered bicyclic carbon rings. Examples include

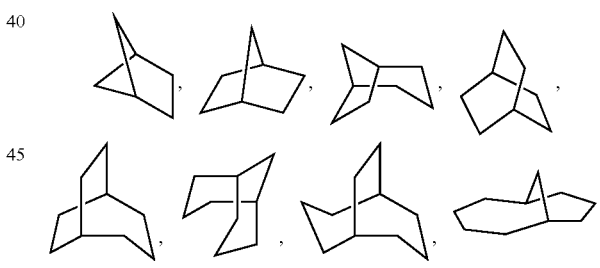

Although already included by the term "heterocycle", the term "bicyclic heterocycles" generally denotes eight-, nine- or ten-membered bicyclic rings which may contain one or more heteroatoms, preferably 1-4, more preferably 1-3, even more preferably 1-2, particularly one heteroatom, selected from among oxygen, sulphur and nitrogen. The ring may be linked to the molecule through a carbon atom of the ring or through a nitrogen atom of the ring, if there is one. Examples include:

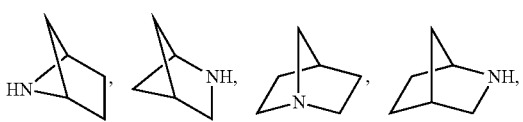

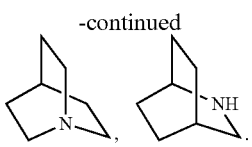

Although already included by the term "aryl", the term "bicyclic aryl" denotes a 5-10 membered, bicyclic aryl ring which contains sufficient conjugated double bonds to form an aromatic system. One example of a bicyclic aryl is naphthyl.

Although already included under "heteroaryl", the term "bicyclic heteroaryl" denotes a 5-10 membered, bicyclic heteroaryl ring which may contain one, two, three or four heteroatoms, selected from among oxygen, sulphur and nitrogen, and contains sufficient conjugated double bonds to form an aromatic system.

Although included by the term "bicyclic cycloalkyls" or "bicyclic aryl", the term "fused cycloalkyl" or "fused aryl" denotes bicyclic rings wherein the bridge separating the rings denotes a direct single bond. The following are examples of a fused, bicyclic cycloalkyl:

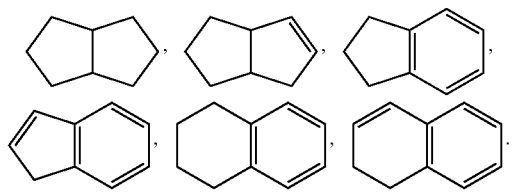

Although included by the term "bicyclic heterocycles" or "bicyclic heteroaryls", the term "fused bicyclic heterocycles" of "fused bicyclic heteroaryls" denotes bicyclic 5-10 membered heterorings which contain one, two, three or four heteroatoms, selected from among oxygen, sulphur and nitrogen and wherein the bridge separating the rings denotes a direct single bond. The "fused bicyclic heteroaryls" moreover contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

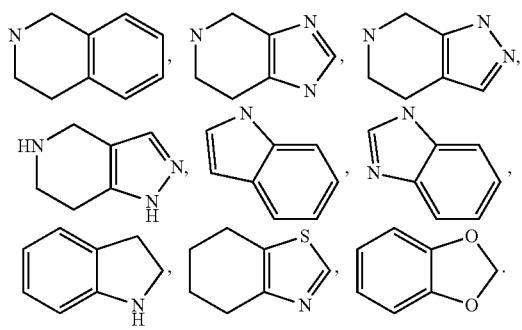

By the term "spiro group" (spiro) are meant 5-10 membered, spirocyclic rings which may optionally contain one, two or three heteroatoms, selected from among oxygen, sulphur and nitrogen, while the ring may be linked to the molecule through a carbon atom or if available through a nitrogen atom. Unless otherwise mentioned, a spirocyclic ring may be provided with an oxo, methyl or ethyl group. Examples of this include:

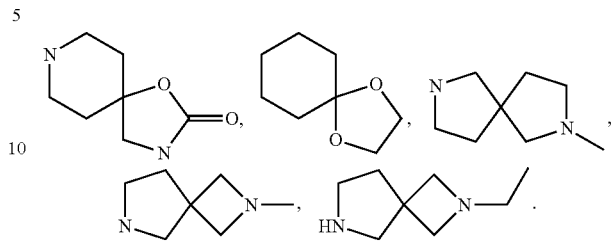

"Halogen" within the scope of the present invention denotes fluorine, chlorine, bromine or iodine. Unless stated to the contrary, fluorine, chlorine and bromine are regarded as preferred halogens.

Compounds of general formula 1 may have acid groups, mainly carboxyl groups, and/or basic groups such as e.g. Amino functions. Compounds of general formula 1 may therefore be present as internal salts, as salts with pharmaceutically usable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically usable bases such as alkali metal or alkaline earth metal hydroxides or carbonates, zinc or ammonium hydroxides or organic amines such as e.g. diethylamine, triethylamine, triethanolamine, inter alia.

As mentioned previously, the compounds of formula 1 may be converted into the salts thereof, particularly for pharmaceutical use into the physiologically and pharmacologically acceptable salts thereof. These salts may be present on the one hand as physiologically and pharmacologically acceptable acid addition salts of the compounds of formula 1 with inorganic or organic acids. On the other hand, the compound of formula 1 when R is hydrogen may be converted by reaction with inorganic bases into physiologically and pharmacologically acceptable salts with alkali or alkaline earth metal cations as counter-ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. To prepare the alkali and alkaline earth metal salts of the compound of formula 1 wherein R denotes hydrogen, it is preferable to use the alkali and alkaline earth metal hydroxides and hydrides, of which the hydroxides and hydrides of the alkali metals, particularly sodium and potassium, are preferred, while sodium and potassium hydroxide are particularly preferred.

The compounds of general formula 1 may optionally be converted into the salts thereof, particularly for pharmaceutical use into the pharmacologically acceptable acid addition salts with an inorganic or organic acid. Examples of suitable acids for this purpose include succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The compounds according to the invention may optionally be present as racemates, but may also be obtained as pure enantiomers, i.e. in the (R) or (S) form.

The invention relates to the compounds in question, optionally in the form of the individual optical isomers, diastereomers, mixtures of diastereomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The invention relates to the respective compounds of formula 1 in the form of the pharmacologically acceptable salts thereof. These pharmacologically acceptable salts of the compounds of formula 1 may also be present in the form of their respective hydrates (e.g. Monohydrates, dihydrates, etc.) as well as in the form of their respective solvates. By a hydrate of the compound according to the formula 1 is meant, for the purposes of the invention, a crystalline salt of the compound according to formula 1, containing water of crystallisation.

By a solvate of the compound according to formula 1 is meant, for the purposes of the invention, a crystalline salt of the compound according to formula 1, which contains solvent molecules (e.g. Ethanol, methanol etc) in the crystal lattice.

The skilled man will be familiar with the standard methods of obtaining hydrates and solvates (e.g. recrystallisation from the corresponding solvent or from water).

4. METHODS OF PREPARATION

The compounds 1 claimed may be prepared by known methods (e.g. WO 03/057695). The Examples according to the invention were prepared according to Scheme 1.

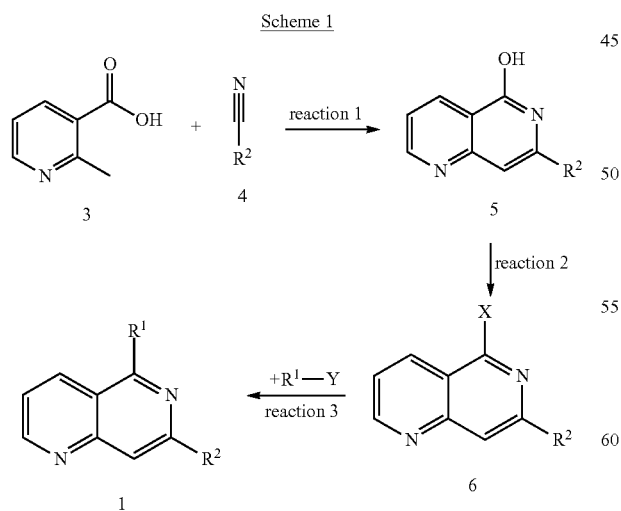

wherein X is a leaving group such as e.g. Cl or triflate, Y is —H, —MgBr, —B(OH)$_2$ and R$^1$ and R$^2$ are as hereinbefore defined.

Optionally the groups R$^1$ or R$^2$ may subsequently be changed e.g. by reductive amination or amide linking.

4.1. Intermediate Products

4.1.1. Synthesis of the Compounds 4 from Scheme 1 (Benzonitrile Derivatives)

Synthesis of 4-dimethylamino-3-methyl-benzonitrile (4.1)

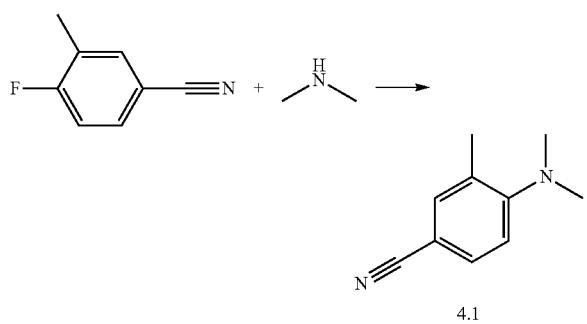

11.0 g (242 mmol) dimethylamine was piped into 100 ml dimethylsulphoxide up to the solubility limit, then 22.0 g (156 mmol) potassium carbonate and 10.0 g (74 mmol) 4-fluoro-3-methyl-benzonitrile were added. The reaction mixture was stirred for 4 h at 60° C., then transferred into a large pressurised flask and another 9.0 g (198 mmol) dimethylamine were piped in. The reaction mixture was stirred overnight at 85° C.

A further 10.0 g (220 mmol) dimethylamine were piped in and then the mixture was stirred for 4 h at 85° C. and overnight at 110° C.

500 ml ice water was added to the reaction mixture, then it was extracted 3 times with 250 ml ethyl acetate, the org. phase was dried, filtered and the solvent was eliminated from the filtrate.

Yield: 12.0 g (75 mmol=101% of theory)

Analysis: HPLC-MS (method D): R$_t$: 0.94 min, (M+H)$^+$: 161

4.1.2. Synthesis of R$^1$ Derivatives (Amine Derivatives)

Synthesis of 4-(2-aminoethyl)-3-hydroxy-1H-pyrazole (for Example 8)

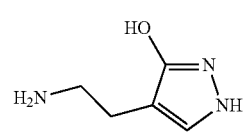

4-(2-aminoethyl)-3-hydroxy-1H-pyrazole was prepared by the following method: Kralj, David; Groselj, Uros; Meden, Anton; Dahmann, Georg; Stanovnik, Branko; Svete, Jurij. A simple synthesis of 4-(2-aminoethyl)-5-hydroxy-1H-pyrazoles. *Tetrahedron* (2007), 63 (45), 11213-11222.

Synthesis of tert-butyl 4-(2-hydroxy-ethyl)-pyrazole-1-carboxylate (for Example 12)

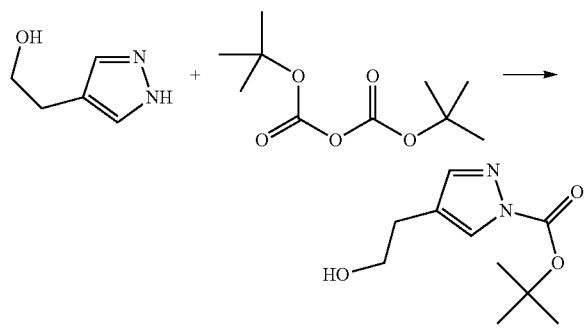

1.10 g (9.81 mmol) 2-(1H-pyrazol-4-yl)-ethanol, 0.20 g (1.64 mmol) 4-dimethylaminopyridine and 1.50 ml (10.3 mmol) triethylamine were placed in 30 ml dichloromethane, the reaction mixture was cooled to 0° C. and 2.20 g (9.88 mmol) tert. butyl carbonate was slowly added. The mixture was stirred for 2 h at ambient temperature and then overnight at ambient temperature. It was diluted with 50 ml dichloromethane and washed with 10% citric acid solution and 15% potassium carbonate solution, the organic phase was dried, filtered and the solvent was eliminated from the filtrate.

Yield: 2.00 g (9.42 mmol=96% of theory)

4.2. Reaction 1 of Scheme 1: Synthesis of Compounds of Formula 5

Synthesis of 7-(4-dimethylamino-3-methylphenyl)-[1,6]naphthyridin-5-ol (5.1)

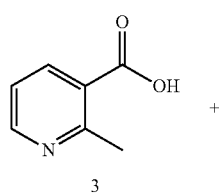

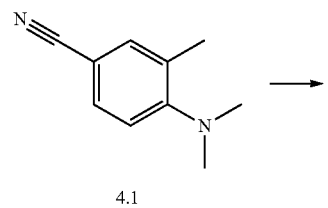

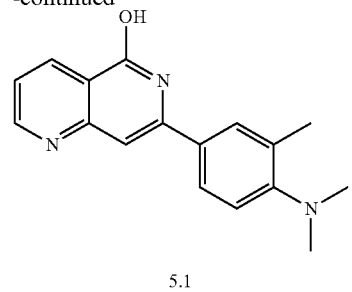

The reaction was carried out under an argon atmosphere.

4.40 g (31 mmol) 2-methyl-nicotinic acid was suspended in 75 ml of tetrahydrofuran, and the mixture was cooled to −80° C. 49 ml (98 mmol) lithium diisopropylamide (2.0 mol/l in tetrahydrofuran) was added dropwise within 30 minutes and the mixture was stirred for 2 h at −60° C.

Then at −60° C. a solution of 5.0 g (31 mmol) 4-dimethylamino-3-methylbenzonitrile in tetrahydrofuran was again added dropwise within 30 minutes. Then the reaction mixture was stirred for 4 h at 0° C.

The suspension was combined with 100 ml of water and the solvent was distilled off.

The aqueous residue was mixed with 20 ml ethyl acetate and stirred for 20 min, then the precipitate was suction filtered and dried.

Yield: 3.0 g (10.70 mmol=34% of theoretical)

Analysis: HPLC (method D): $R_t$=0.96 min. ESI-MS: $(M+H)^+$: 280

4.3. Reaction 2 of Scheme 1: Synthesis of Compounds of Formula 6

4.3.1 Synthesis of 5-chloro-7-(4-dimethylamino-3-methylphenyl)-[1,6]naphthyridine (6.1)

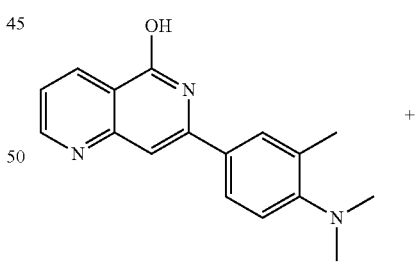

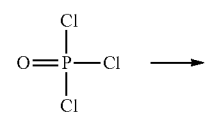

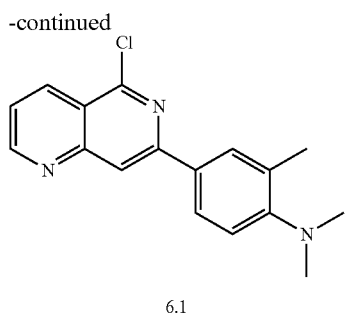

6.1

3.0 g (10.7 mmol) 5.1 and 0.50 ml (2.3 mmol) N,N-diethylaniline were stirred in 25 ml (272 mmol) phosphorus oxychloride for 1 h at 115° C.

The reaction mixture was evaporated down, the residue was mixed with approx. 50 ml of water, made neutral with NaHCO₃ solution and extracted with dichloromethane. The organic phase was dried with MgSO₄ and evaporated down.

Yield: 1.90 g oil (4.7 mmol=44% of theoretical)

Analysis: HPLC (method D): $R_f$=1.25 min. ESI-MS: (M+H)⁺: 298/300 (Cl)

4.3.2. Synthesis of 7-(4-dimethylamino-3-methylphenyl)-[1,6]naphthyridin-5-yl-trifluoromethanesulphonic acid ester (6.2)

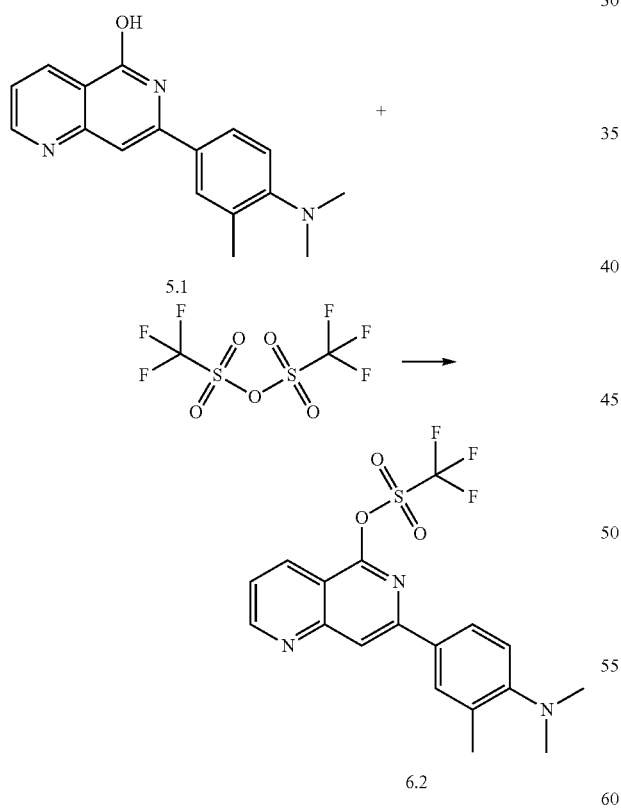

2.2 mL (12 mmol) trifluoromethanesulphonic acid anhydride was placed in 25 mL dichloromethane and while cooling with ice, 3.40 g (12 mmol) 5.1, dissolved in 1.1 ml (13 mmol) pyridine and 25 mL dichloromethane, were added dropwise. After this addition the reaction mixture was heated to ambient temperature and stirred overnight at 25° C.

Then another 1.5 ml of trifluoromethanesulphonic acid anhydride and 3 mL of pyridine were added. After an hour the mixture was diluted with 100 mL ice water, the organic phase was washed with NaCl solution, dried with MgSO₄ and evaporated down. The residue was taken up in toluene twice more and then evaporated down.

Yield: 4.70 g (8.4 mmol=69% of theory)

Analysis: HPLC (method D): $R_f$=1.40 min ESI-MS (M+H)⁺=412

4.4. Reaction 3 of Scheme 1 (Synthesis of the Examples of Formula 1)

Examples 1+2 cis and trans 5-(4-hydroxycyclohexyl)-7-(4-dimethylamino-3-methylphenyl)-[1,6]naphthyridine

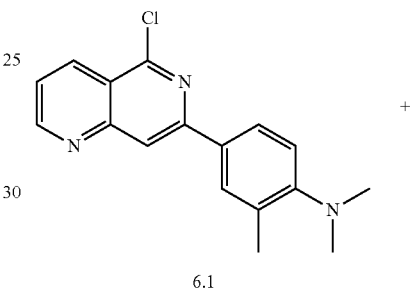

6.1

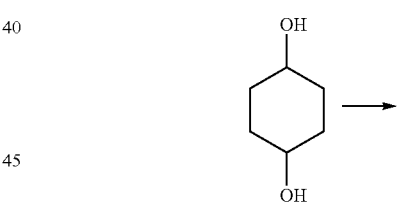

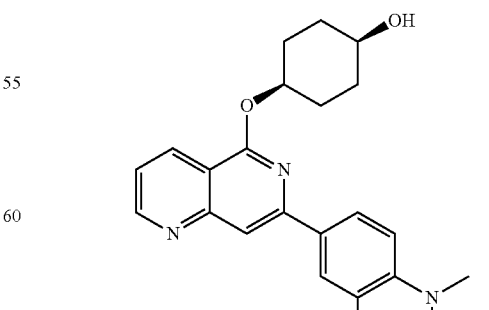

Example 1

-continued

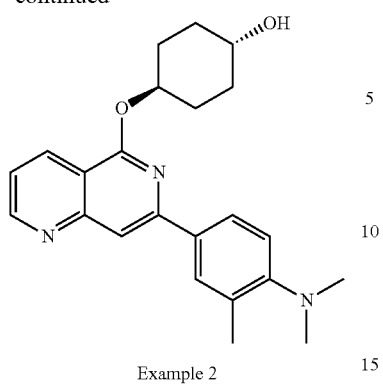

Example 2

200 mg (1.7 mmol) cyclohexanediol was placed in 1.5 ml dimethylacetamide and 47 mg (1.17 mmol) sodium hydride (60%) were added and the mixture was stirred for 15 min at ambient temperature. Then 100 mg (0.31 mmol) 6.1 was added and the mixture was stirred for 2 h at 70° C. The reaction mixture was diluted with dichloromethane and extracted 1× with water. The organic phase was dried with MgSO$_4$ and evaporated down. The residue was purified by chromatography (RP-HPLC-MS). The corresponding fractions were freeze-dried.

Yield Example 1: 9 mg (0.018 mmol=5.5% of theory)

Analysis: HPLC-MS (method D): R$_t$: 1.13 min, (M+H)$^+$: 378

Yield Example 2: 42 mg (0.085 mmol=25% of theory)

Analysis: HPLC-MS (method D): R$_t$: 1.15 min, (M+H)$^+$: 378

Example 7 was prepared analogously to Examples 1+2.

Example 3

5-(aminomethylpyrrolidin-1-yl)-7-(4-dimethylamino-3-methylphenyl)-[1,6]naphthyridine

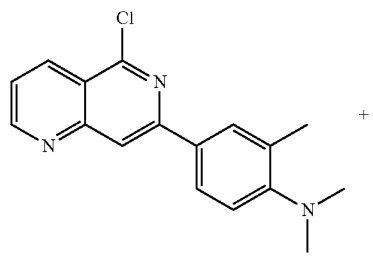

6.1

+

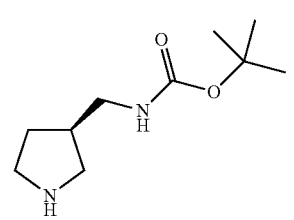

-continued

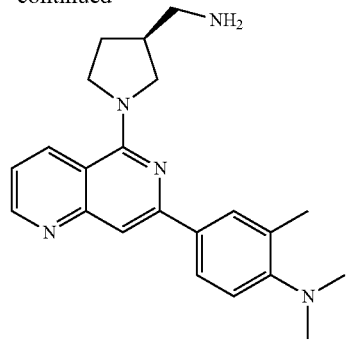

Example 3

100 mg (0.37 mmol) 6.1 was stirred with 210 mg (1.04 mmol) of (R)-3-N-tert-butyloxycarbonyl-aminomethylpyrrolidine for 60 min at 100° C. 1 ml trifluoroacetic acid and acetonitrile were added to the mixture and it was stirred for 30 min at 50° C. It was diluted with acetonitrile/water and purified by chromatography (RP-HPLC-MS). The corresponding fractions were freeze-dried.

Yield: 120 mg (0.33 mmol=99% of theory)

Analysis: HPLC-MS (method D): R$_t$: 1.00 min, (M+H)$^+$: 362

Example 4

5-(pyrrolidin-3-yl-methoxy)-7-(4-dimethylamino-3-methylphenyl)-[1,6]naphthyridine

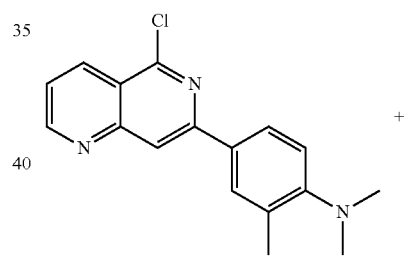

6.1

+

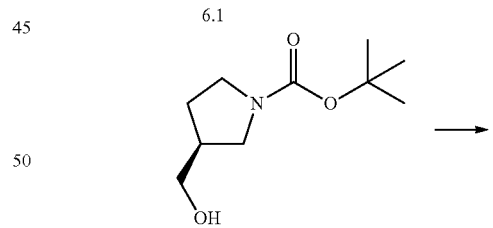

→

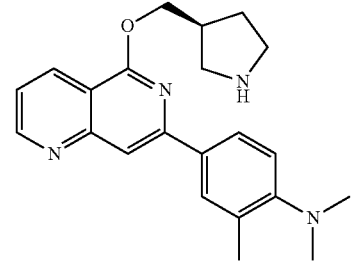

Example 4

118 mg (0.59 mmol) tert.butyl(S)-3-hydroxymethylpyrrolidinecarboxylate and 23.5 mg (0.59 mmol) sodium hydride (60%) were placed in 0.5 ml dimethylacetamide and stirred for 15 min at ambient temperature. Then 70 mg (0.24 mmol) of 6.1 was added and the mixture was stirred for 2 h at 70° C.

1 mL of trifluoroacetic acid was added and the mixture was stirred for 2 days at 25° C. The reaction mixture was purified by chromatography (RP-HPLC-MS). The corresponding fractions were freeze-dried.

Yield: 110 mg (0.23 mmol=98% of theory)
Analysis: HPLC-MS (method D): R$_t$: 1.05 min, (M+H)$^+$: 363

The following compounds were obtained analogously to Example 4: Example 14, 15, 18, 19.

Example 6

5-(3-pyrazolyl-ethylamino)-7-(4-dimethylamino-3-methylphenyl)-[1,6]naphthyridine

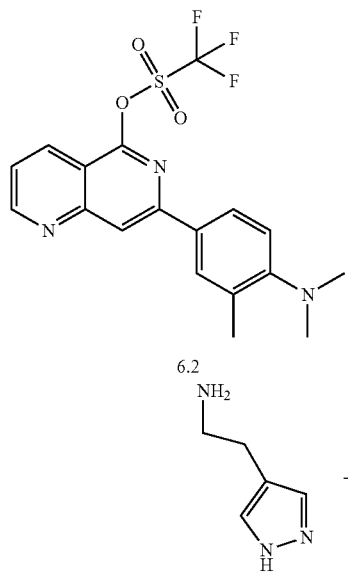

Example 6

100 mg (0.18 mmol) of 6.2, 65 mg (0.35 mmol) of 2-(1H-pyrazol-4-yl)ethylamine dihydrochloride and 120 µl (0.71 mmol) diisopropylethylamine were stirred in 0.5 ml of dimethylacetamide for 2 h at 80° C.

The mixture was purified by chromatography (RP-HPLC-MS). The corresponding fractions were freeze-dried.

Yield: 70.00 mg (0.14 mmol=81% of theory)
Analysis: HPLC-MS (method D): R$_t$: 1.05 min, (M+H)$^+$: 373

Examples 8-11, 13, 22, 24-30 were obtained analogously to Example 6.

Example 12

5-(4-hydroxyethyl-pyrazolyl)-7-(4-dimetyhlamino-3-methylphenyl)-[1,6]naphthyridine

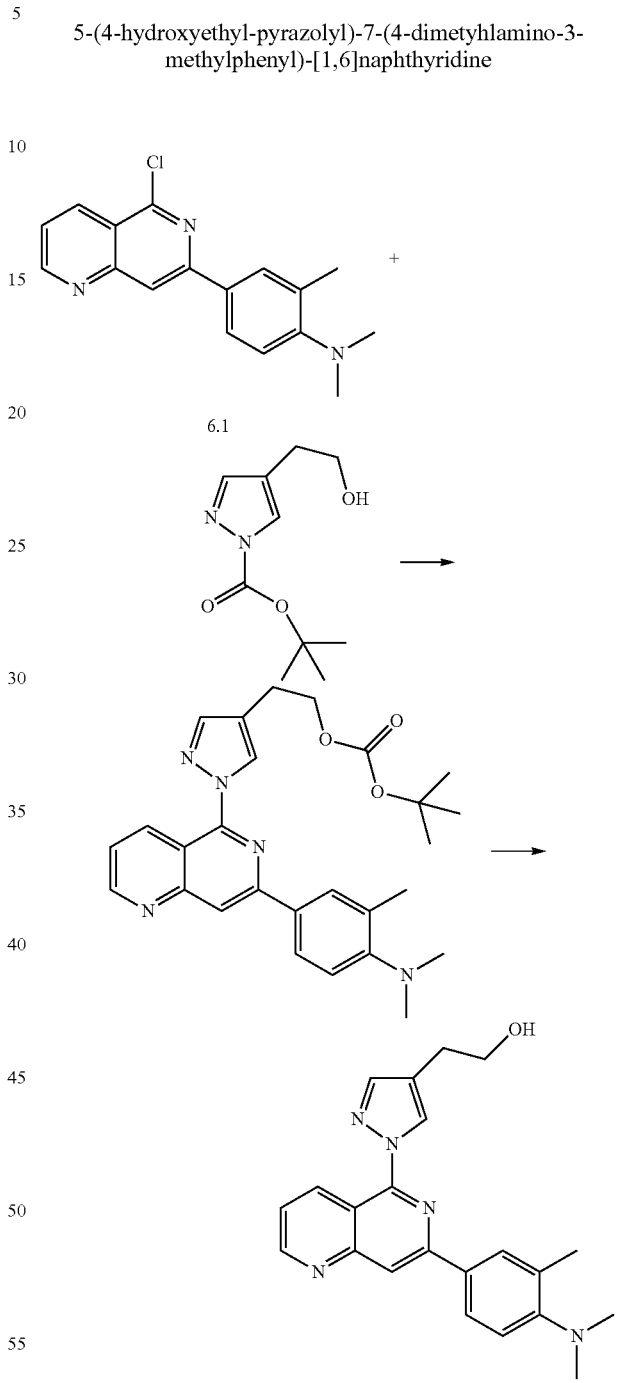

Example 12

110 mg (0.49 mmol) of tert.butyl 4-(2-hydroxy-ethyl)-pyrazole-1-carboxylate was dissolved in 0.5 mL dimethylacetamide, 22 mg (0.5 mmol) of NaH (55%) were added and the mixture was stirred for 15 min. Then 100 mg (0.34 mmol) 6.1 was added and the mixture was stirred for 1 h at 50° C. The mixture was diluted with acetonitrile, water and trifluoroacetic acid and purified by chromatography (RP-HPLC).

Yield: 50 mg (0.11 mmol=31% of theory).

Analysis: HPLC-MS (method D): $R_t$: 1.45 min, $(M+H)^+$: 474

50 mg (0.11 mmol) tert-butyl-2-{1-[7-(4-dimethylamino-3-methyl-phenyl)-[1,6]naphthyridin-5-yl]-1H-pyrazol-4-yl}-carbonate was dissolved in 2 ml (8 mmol) dioxanic hydrochloric acid (4 mol/l) and stirred for 2 h at 50° C. The reaction mixture was evaporated down, the residue was purified by chromatography (RP-HPLC-MS), the corresponding fractions were freeze-dried.

Yield: 30 mg (0.08 mmol=76% of theory)

Analysis: HPLC-MS (method D): $R_t$: 1.17 min, $(M+H)^+$: 374

Example 17

5-methoxy-7-(4-dimethylamino-3-methylphenyl)-[1,6]naphthyridine

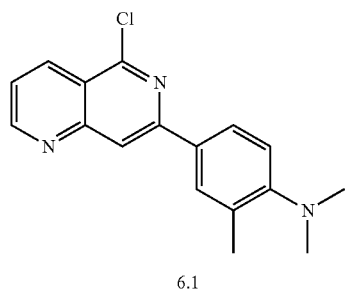

6.1

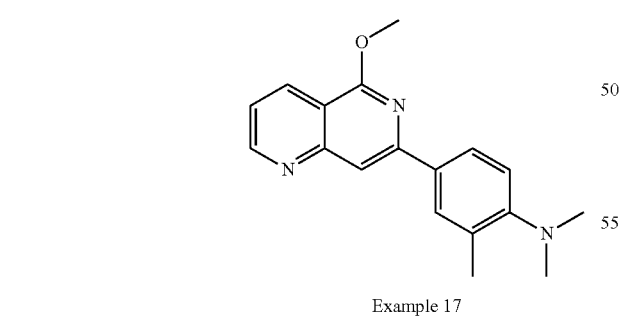

Example 17

100 mg (0.31 mmol) of 6.1 was placed in 0.5 ml dimethylacetamide and then 60 mg (1.1 mmol) sodium methoxide were added. The reaction mixture was stirred for 1 h at 50° C.

The mixture was purified by chromatography (RP-HPLC-MS), the corresponding fractions were freeze-dried.

Yield: 120 mg (0.29 mmol=88% of theory)

Analysis: HPLC-MS (method D): $R_t$: 1.14 min, $(M+H)^+$: 294

Example 20

5-(cyclopropylamino)-7-(4-dimethylamino-3-methylphenyl)-[1,6]naphthyridine

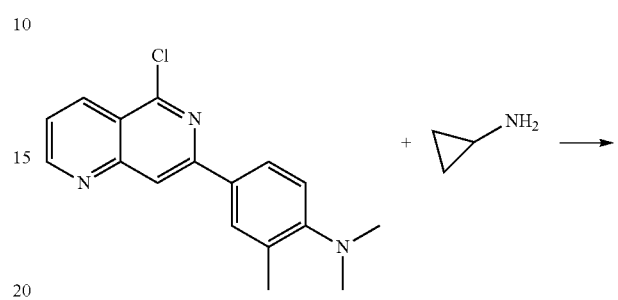

6.1

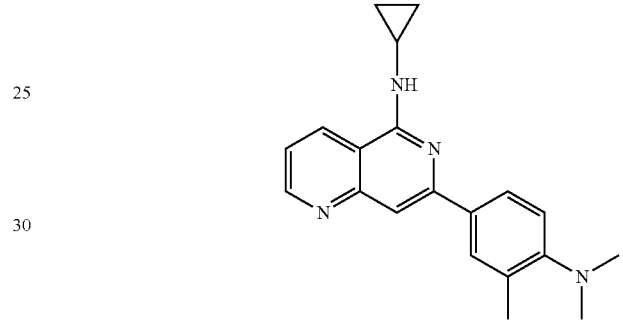

Example 20

100 mg (0.34 mmol) 6.1, 75 µL (1.07 mmol) cyclopropylamine were dissolved in 500 µl dimethylformamide and stirred overnight at 100° C. The mixture was combined with acetonitrile/water and trifluoroacetic acid and purified by chromatography (RP-HPLC). The corresponding fractions were freeze-dried.

Yield: 40 mg (0.131 mmol=40% of theory)

Analysis: HPLC-MS (method D): $R_t$: 1.07 min, $(M+H)^+$: 319

Examples 5, 16 were obtained analogously to Example 20.

Example 21

5-(pyrrolidin-2-on-4-yl-methylhydroxy)-7-(4-dimethylamino-3-methylphenyl)-[1,6]naphthyridine

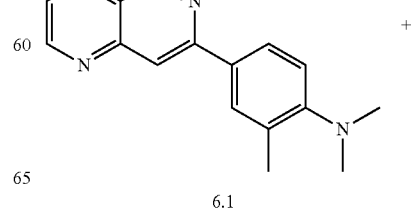

6.1

-continued

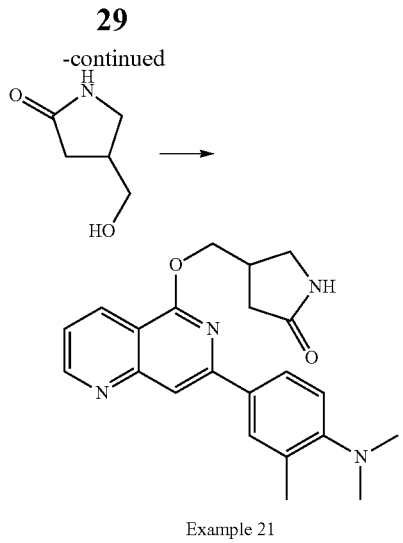

Example 21

45 mg (0.38 mmol) 4-hydroxymethylpyrrolidin-2-one was placed in 1 ml dimethylacetamide and 16 mg (0.29 mmol) sodium hydride (60%) were added and the mixture was stirred for 15 min at ambient temperature. Then 100 mg (0.34 mmol) of 6.1 was added and the mixture was stirred for 2 h at 50° C. and overnight at 25° C. The reaction mixture was purified by chromatography (RP-HPLC-MS). The corresponding fractions were freeze-dried.

Yield: 120 mg (0.32 mmol=95% of theory)

Analysis: HPLC-MS (method D): $R_t$: 1.09 min, $(M+H)^+$: 377

Example 23 was obtained analogously to Example 21.

4.5 Chromatographic Methods (HPLC-MS Methods)

The compounds by way of example prepared according to the above synthesis schemes were characterised by the following chromatographic method, which—if carried out—are individually specified in Table 1.

Method D

Waters ZMD, Alliance 2690/2695 HPLC, Waters 996/2996 diode array detector

The mobile phase used was:

A: water with 0.10% TFA

B: acetonitrile with 0.10% TFA

| time in min | % A | % B | flow rate in ml/min |
| --- | --- | --- | --- |
| 0.00 | 95 | 5 | 2.80 |
| 0.30 | 95 | 5 | 2.80 |
| 1.60 | 2 | 98 | 2.80 |
| 1.90 | 2 | 98 | 2.80 |
| 2.00 | 95 | 5 | 2.50 |

The stationary phase used is a Merck Chromolith™ Flash RP-18e column, 3 mm×100 mm (column temperature: constant at 25° C.).

Diode array detection was carried out in the wavelength range from 210-400 nm.

5. EXAMPLES

The following Examples were prepared analogously to the methods of synthesis described above (as indicated in Table 1). These compounds are suitable as SYK inhibitors and have $IC_{50}$ values of less than or equal to 1 μmol. The inhibitions (in %) at 1 μM of the individual example substances are shown in the following Table of Examples and were determined as follows:

Syk Kinase Test

Recombinant human Syk was expressed as a fusion protein with an N-terminal GST tag, affinity-purified and deep-frozen at a concentration of approx. 50-100 μM in the test buffer (25 mM HEPES pH7.5; 25 mM $MgCl_2$; 5 mM $MnCl_2$; 50 mM KCl; 0.2% BSA; 0.01% CHAPS; 100 μM $Na_3VO_4$; 0.5 mM DTT) and 10% glycerol at −80° C. until wanted for use.

The catalytic activity of the GST-Syk kinase fusion protein was determined using the Kinase Glo® Luminescence Kinase test of Messrs Promega. In this homogeneous test the amount of ATP remaining after the kinase reaction has been carried out is quantified by a luciferin-luciferase reaction using luminescence. The luminescence signal obtained correlates with the amount of ATP still present and thus correlates inversely with the activity of the protein kinase.

Method

The test substances were dissolved in 100% DMSO at a concentration of 10 mM and diluted in DMSO to a concentration of 1 mM. All further dilutions of the substances were carried out with 7.5% DMSO in test buffer until a concentration was reached which was 7.5 times above the final test concentration (final concentration of the substances: in normal cases 30 μM to 1 nM). 2 μl aliquots of these dilutions were transferred into a 384-well Optiplate (Perkin Elmer, #6007290). GST-Syk was diluted to 6.0 nM in the test buffer and 10 μl of this dilution were used in the kinase test (final concentration of Syk=4 nM in a total volume of 15 μl). After 15 minutes' incubation at ambient temperature 3 μl of a mixture of 750 nM ATP and 100 μg/ml poly (L-Glutamic acid L-Tyrosine 4:1), Fluka #81357) in test buffer were added to each well and then incubation was continued for a further 60 minutes at ambient temperature.

Positive controls are the reaction mixtures that contain no test substance; negative controls are reaction mixtures that contain no kinase.

After 60 minutes, 10 μl Kinase-Glo® solution (Promega, Cat. #V6712) (heated to ambient temperature) are added to each well and incubation is continued for a further 15 minutes at ambient temperature. Then the plates are read in a Microplate Scintillation and Luminescence Counter (PerkinElmer/Wallac: MicroBeta TRILUX 1450 LSC & Luminescence Counter).

Data Evaluation and Calculation:

The output file of the "MicroBeta TRILUX" is a text file that contains the well number and measurements obtained. For evaluation, the measurement of the negative control was set as 100% inhibition and the measurement of the positive control was set as 0% inhibition. Then from this the % inherent value for the measurement of each substance concentration was calculated using an "MS-Excel—VB macro". Normally, the % inhibition values calculated are between 100% and 0% inhibition, but in individual cases values may also occur outside these limits. The $IC_{50}$ values were calculated from the % inhibition values using "GraphPadPrism" software (Version 5) (GraphPad Software Inc.).

TABLE 1

Examples of formula 1

The following Examples of formula 1

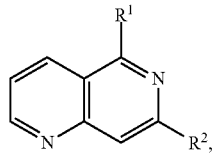

having the following properties were prepared according to the methods of synthesis described above, wherein $X_1$ denotes the point where the group $R^1$ is linked to the structure of formula 1, and wherein $X_2$ denotes the point where the group $R^2$ is linked to the structure of formula 1:

| Ex | $R^1$ | $R^2$ | retention times | SYK inh % at 1 µM | preparation method |
|---|---|---|---|---|---|
| 1 | cis-4-(X₁O)cyclohexyl-OH | 2-methyl-4-(X₂)-N,N-dimethylaniline | 1.13 | 85.2 | see description |
| 2 | trans-4-(X₁O)cyclohexyl-OH | 2-methyl-4-(X₂)-N,N-dimethylaniline | 1.15 | 71.9 | see description |
| 3 | 1-X₁-3-(aminomethyl)pyrrolidine | 2-methyl-4-(X₂)-N,N-dimethylaniline | 0.99 | 88.2 | see description |
| 4 | 3-(X₁OCH₂)pyrrolidine | 2-methyl-4-(X₂)-N,N-dimethylaniline | 1.05 | 87.5 | see description |
| 5 | X₁-NH-ethyl | 2-methyl-4-(X₂)-N,N-dimethylaniline | 1.07 | 97.8 | analogously to Example 20 |
| 6 | X₁-NH-CH₂CH₂-(1H-pyrazol-4-yl) | 2-methyl-4-(X₂)-N,N-dimethylaniline | 1.05 | 85.2 | see description |
| 7 | X₁-O-CH₂CH₂-(1H-pyrazol-4-yl) | 2-methyl-4-(X₂)-N,N-dimethylaniline | 1.13 | 71.9 | analogously to Example 1 |

TABLE 1-continued

Examples of formula 1

The following Examples of formula 1

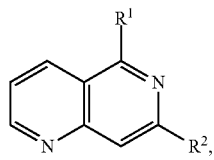

having the following properties were prepared according to the methods of synthesis described above, wherein $X_1$ denotes the point where the group $R^1$ is linked to the structure of formula 1, and wherein $X_2$ denotes the point where the group $R^2$ is linked to the structure of formula 1:

| Ex | $R^1$ | $R^2$ | retention times | SYK inh % at 1 μM | preparation method |
|---|---|---|---|---|---|
| 8 | | | 1.06 | 88.2 | analogously to Example 6 |
| 9 | | | 1.01 | 87.5 | analogously to Example 6 |
| 10 | | | 1.11 | 102 | analogously to Example 6 |
| 11 | | | 1.06 | 97.8 | analogously to Example 6 |
| 12 | | | 1.17 | 105 | see description |
| 13 | | | 1.04 | 90.5 | analogously to Example 6 |

TABLE 1-continued

Examples of formula 1

The following Examples of formula 1

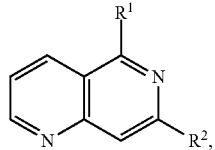

having the following properties were prepared according to the methods of synthesis described above, wherein $X_1$ denotes the point where the group $R^1$ is linked to the structure of formula 1, and wherein $X_2$ denotes the point where the group $R^2$ is linked to the structure of formula 1:

| Ex | $R^1$ | $R^2$ | retention times | SYK inh % at 1 μM | preparation method |
|---|---|---|---|---|---|
| 14 | | | 1.02 | 90.6 | analogously to Example 4 |
| 15 | | | 1.02 | 73.4 | analogously to Example 4 |
| 16 | | | 0.99 | 81.4 | analogously to Example 20 |
| 17 | | | 1.14 | 73.2 | see description |
| 18 | | | 1.06 | 68 | analogously to Example 4 |
| 19 | | | 1.01 | 85.8 | analogously to Example 4 |

TABLE 1-continued

Examples of formula 1

The following Examples of formula 1

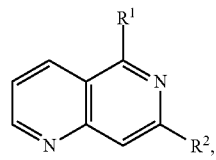

having the following properties were prepared according to the methods of synthesis described above, wherein $X_1$ denotes the point where the group $R^1$ is linked to the structure of formula 1, and wherein $X_2$ denotes the point where the group $R^2$ is linked to the structure of formula 1:

| Ex | $R^1$ | $R^2$ | retention times | SYK inh % at 1 μM | preparation method |
|---|---|---|---|---|---|
| 20 | | | 1.07 | 90.2 | see description |
| 21 | | | 1.09 | 92.9 | see description |
| 22 | | | 1.00 | 90.1 | analogously to Example 6 |
| 23 | | | 1.34 | 80.5 | analogously to Example 21 |
| 24 | | | 1.14 | 93.3 | analogously to Example 6 |
| 25 | | | 1.17 | 97.6 | analogously to Example 6 |
| 26 | | | 1.02 | 87.5 | analogously to Example 6 |

TABLE 1-continued

Examples of formula 1

The following Examples of formula 1

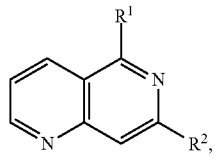

having the following properties were prepared according to the methods of synthesis described above, wherein $X_1$ denotes the point where the group $R^1$ is linked to the structure of formula 1, and wherein $X_2$ denotes the point where the group $R^2$ is linked to the structure of formula 1:

| Ex | $R^1$ | $R^2$ | retention times | SYK inh % at 1 μM | preparation method |
|---|---|---|---|---|---|
| 27 | (pyrazolyl-CH2-NH-X1) | (dimethylamino-methylphenyl-X2) | 1.05 | 88.7 | analogously to Example 6 |
| 28 | (pyrrolidinone-CH2-NH-X1) | (dimethylamino-methylphenyl-X2) | 1.02 | 95.9 | analogously to Example 6 |
| 29 | (indazolyl-NH-X1) | (dimethylamino-methylphenyl-X2) | 1.14 | 63 | analogously to Example 6 |
| 30 | (tetrahydropyrazolopyridinyl-X1) | (dimethylamino-methylphenyl-X2) | 1.07 | 80.6 | analogously to Example 6 |

6. INDICATIONS

As has been found, the compounds of formula 1 are characterised by their range of applications in the therapeutic field. Particular mention should be made of those applications for which the compounds of formula 1 according to the invention are preferably used on the basis of their pharmaceutical activity as SYK-inhibitors. Examples include respiratory complaints, allergic diseases, osteoporosis, gastrointestinal diseases or complaints, immune or autoimmune diseases, allergic diseases, inflammatory diseases, e.g. inflammatory diseases of the joints, skin and eyes and diseases of the peripheral or central nervous system.

Particular mention should be made of the prevention and treatment of respiratory tract and pulmonary diseases which are accompanied by increased mucus production, inflammation and/or obstructive diseases of the airways. Examples of these include asthma, paediatrich asthma, ARDS (Adult Respiratory Distress Syndrome), acute, allergic or chronic bronchitis, chronic obstructive bronchitis (COPD) (including the treatment of Rhinovirus-induced exacerbations), coughs, allergic rhinitis or sinusitis, allergic rhinoconjunctivitis, chronic rhinitis or sinusitis, alveolitis, farmers' lung, hyperreactive airways, infectious bronchitis or pneumonitis, bronchiectasis, pulmonary fibrosis, bronchial oedema, pulmonary oedema, pneumonia or interstitial pneumonia triggered by various causes such as aspiration, inhalation of toxic gases or bronchitis, pneumonia or interstitial pneumonia triggered by cardiac insufficiency, radiation, chemotherapy, cystic fibrosis or mucoviscidosis, alpha1-antitrypsin deficiency.

The compounds according to the invention are preferably also suitable for the treatment of allergic diseases such as for example allergic rhinitis, allergic rhinoconjunctivitis, allergic conjunctivitis, allergic dermatitis and contact dermatitis, urticaria/angiooedema and allergic dermatitis.

Mention should also preferably be made of the treatment of inflammatory diseases of the gastrointestinal tract. Examples of these are Crohn's disease and ulcerative colitis.

The compounds according to the invention are preferably also suitable for the treatment of inflammatory diseases of the joints or inflammatory diseases of the skin and eyes. Examples of these are rheumatoid arthritis, antibody-based glomerulonephritis, psoriasis, Kawasaki syndrome, coeliac disease (sprue) and Wegener's granulomatosis.

The compounds according to the invention are preferably also suitable for the treatment of autoimmune diseases. Examples of these are hepatitis (autoimmune-based), lupus erythematodes, anti-phospholipid syndrome, Berger's disease, Evans's syndrome, immunohaemolytic anaemia, ITP (idiopathic thrombocytopenic purpura; adult, neonatal and paediatric), myasthenia gravis, Sjögren's syndrome and sclerodermy.

The compounds according to the invention are preferably also suitable for the treatment of B-cell lymphomas.

Mention may preferably also be made of the prevention and treatment of diseases of the peripheral or central nervous system. Examples of these are acute and chronic multiple sclerosis or non-familial lateral sclerosis.

Mention may preferably also be made of the prevention and treatment of osteoporotic diseases such as for example disease-associated osteopenia, osteoporosis and osteolytic diseases.

The present invention relates particularly preferably to the use of compounds of formula 1 for preparing a pharmaceutical composition for the treatment of diseases selected from among asthma, COPD, allergic rhinitis, Adult Respiratory Distress Syndrome, bronchitis, allergic dermatitis, contact dermatitis, ITP, rheumatoid arthritis and allergic rhinoconjunctivitis.

Most preferably, the compounds of formula 1 may be used for the treatment of a disease selected from among asthma, allergic rhinitis, rheumatoid arthritis, allergic dermatitis and COPD.

7. COMBINATIONS

The compounds of formula 1 may be used on their own or in conjunction with other active substances of formula 1 according to the invention. The compounds of formula 1 may optionally also be used in conjunction with other pharmacologically active substances. Preferably the active substances used here may be selected for example from among the betamimetics, anticholinergics, corticosteroids, PDE4-inhibitors, LTD4-antagonists, EGFR-inhibitors, MRP4-inhibitors, dopamine agonists, H1-antihistamines, PAF-antagonists, iNos-inhibitors, PI3-kinase-inhibitors, CCR3-antagonists, CCR2-antagonists, CCR1-antagonists, IKK2-inhibitors, A2a agonists, alpha-4-integrin-inhibitors, CRTH2-antagonists, histamine 1, combined H1/H3-antagonists, p38 kinase inhibitors, methylxanthines, ENaC-inhibitors, CXCR1-antagonists, CXCR2-antagonists, ICE-inhibitors, LTB4-antagonists, 5-LO antagonists, FLAP-antagonists. LTB4-antagonists; cromoglycine, dissociated glucocorticoid mimetics, anti-TNF-antibodies, anti-GM-CSF antibodies, anti-CD46-antibodies, anti-IL-1-antibodies, anti-IL-2-antibodies, anti-IL-4-antibodies, anti-IL-5-antibodies, anti-IL-13-antibodies, anti-IL-4/IL-13-antibodies, or double or triple combinations thereof, such as for example combinations of compounds of formula 1 with one or two compounds selected from among the betamimetics, corticosteroids, SYK-inhibitors of formula 1, EGFR-inhibitors and PDE4-antagonists, anticholinergics, betamimetics, corticosteroids, SYK-inhibitors of formula 1, EGFR-inhibitors and PDE4-antagonists, PDE4-inhibitors, corticosteroids, EGFR-inhibitors and SYK-inhibitors of formula 1, EGFR-inhibitors, PDE4-inhibitors and SYK-inhibitors of formula 1

EGFR-inhibitors and SYK-inhibitors of formula 1

SYK-inhibitors of formula 1, betamimetics and anticholinergics anticholinergics, betamimetics, corticosteroids, PDE4-inhibitors and SYK-inhibitors of formula 1.

Combinations of three active substances each taken from one of the above-mentioned categories of compounds are also an object of the invention.

Suitable betamimetics used are preferably compounds selected from among albuterol, bambuterol, bitolterol, broxaterol, carbuterol, carmoterol, indacaterol, clenbuterol, fenoterol, formoterol, arformoterol, zinterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2 (3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxy-carbonylamino-3-cyano-5-fluorophenyl)-2-(tert.-butylamino)ethanol, optionally in the form of the racemates, enantiomers, diastereomers and optionally in the form of the pharmacologically acceptable acid addition salts, solvates or hydrates thereof.

Of these betamimetics the particularly preferred ones according to the invention are formoterol, salmeterol, 3-(4-{6-[2-hydroxy-2-(4-hydroxy-3-hydroxymethyl-phenyl)-ethylamino]-hexyloxy}-butyl)-benzenesulphonamide, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1.1dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 5-[2-(5,6-diethyl-indan-2-ylamino)-1-hydroxy-ethyl]-8-hydroxy-1H-quinoline-2-one, optionally in the form of the racemates, enantiomers, diastereomers and optionally in the form of the pharmacologically acceptable acid addition salts, solvates or hydrates thereof.

According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among the tiotropium salts, oxitropium salts, flutropium salts, ipratropium salts, glycopyrronium salts, aclidinium bromide, trospium salts, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate-methobromide, tropenol 9-fluoro-fluorene-9-carboxylate-methobromide, scopine 9-hydroxy-fluoren-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl cyclopropyltropine 4,4'-difluorobenzilate methobromide, tropenol 9-hydroxy-xanthene-9-carboxylate-methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide, optionally in the form of the solvates or hydrates thereof.

In the above-mentioned salts the cations tiotropium, oxitropium, flutropium, ipratropium, glycopyrronium, aclidinium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among prednisolone, prednisone, butixocortpropionate, flunisolide, beclomethasone, triamcinolone, budesonide, fluticasone, mometasone, ciclesonide, rofleponide, dexamethasone, betamethasone, deflazacort, RPR-106541, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferably the steroid is selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulfobenzoates, phosphates, isonicotinates, acetates, propionates, dihydrogen phosphates, palmitates, pivalates or furoates thereof.

PDE4 inhibitors which may be used are preferably compounds selected from among enprofyllin, theophyllin, roflumilast, ariflo (cilomilast), tofimilast, pumafentrin, lirimilast, arofyllin, atizoram, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370, N-(3,5-dichloro-1-oxo-pyridin-4-yl)-4-difluoromethoxy-3-cyclopropylmethoxybenzamide, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferably the PDE4-inhibitor is selected from among roflumilast, ariflo (cilomilast), arofyllin, AWD-12-281 (GW-842470), 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], atizoram, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichloro-thieno[3,2-b]pyridin-5-yl)-(E)-ethenyl)phenyl)-3-(2-(1-hydroxy-1-methylethyl)phenyl)-propyl)thio)methyl)cyclopropane-acetic acid and [2-[[2-(4-tert-butyl-2-thiazolyl)-5-benzofuranyl]oxymethyl]phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

Particularly preferably the LTD4-antagonist is selected from among montelukast, pranlukast, zafirlukast, MCC-847 (ZD-3523), MN-001 and MEN-91507 (LM-1507), optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo- 2-buten-1-yl]amino}-7-[(S)-(tetrahydrofuran-2-yl) methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazolin; 4-{2-[4-(3-chloro-4-fluoro-phenylamino)-7-methoxy-quinazolin-6-yloxy]-ethyl}-6-methyl-morpholine-2-one, 4-{4-[4-(3-chloro-2-fluoro-phenylamino)-7-methoxy-quinazolin-6-yloxy]-cyclohexyl}-1-methyl-piperazin-2-one, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-(N-(2-methoxy-acetyl)-N-methyl-amino-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl))carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2.2.1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]- piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, [4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-7-(2-{4-[(S)-(2-oxo-tetrahydrofuran-5-yl)carbonyl]-piperazin-1-yl}-ethoxy)-6-[(vinylcarbonyl)amino]-quinazoline, 4-[(3-chloro-4-fluoro-phenyl)amino]-7-[2-((S)-6-methyl-2-oxo-morpholin-4-yl)-ethoxy]-6-[(vinylcarbonyl)amino]-quinazoline, 4-[(3-chloro-4-fluoro-phenyl)amino]-7-[4-((R)-6-methyl-2-oxo-morpholin-4-yl)-butyloxy]-6-[(vinylcarbonyl)amino]-quinazoline, 4-[(3-chloro-4-fluoro-phenyl)amino]-7-[4-((S)-6-methyl-2-oxo-morpholin-4-yl)-butyloxy]-6-[(vinylcarbonyl)amino]-quinazoline, 4-[(3-chloro-4-fluoro-phenyl)amino]-7-(2-{4-[(S)-(2-oxo-tetrahydrofuran-5-yl)carbonyl]-piperazin-1-yl}-ethoxy)-6-[(vinylcarbonyl)amino]-quinazoline, 4-[(3-chloro-4-fluoro-phenyl)amino]-7-[2-((S)-6-methyl-2-oxo-morpholin-4-yl)-ethoxy]-6-[(vinylcarbonyl)amino]-quinazoline, 4-[(3-chloro-4-fluoro-phenyl)amino]-7-[4-((R)-6-methyl-2-oxo-morpholin-4-yl)-butyloxy]-6-[(vinylcarbonyl)amino]-quinazoline, 4-[(3-chloro-4-fluoro-phenyl)amino]-7-[4-((S)-6-methyl-2-oxo-morpholin-4-yl)-butyloxy]-6-[(vinylcarbonyl)amino]-quinazoline, cetuximab, trastuzumab, ABX-EGF, Mab ICR-62, gefitinib, canertinib and erlotinib, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpholinyl)carbonyl]-4H,7H-cyclo-penta-[4,5]thieno[3,2-f][1,2,4]triazolo[4,3-a][1,4] diazepines. Any reference to the above-mentioned above-mentioned PAF-antagonists includes within the scope of the present invention a reference to any pharmacologically acceptable acid addition salts thereof which may exist.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-beta-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, glycolithocholic acid sulphate, ibuprofen, indomethacin, indoprofen, ketoprofen, lithocholic acid sulphate, methotrexate, MK571 ((E)-3-[[[3-[2-(7-chloro-2-quinolinyl)ethenyl]phenyl]-[[3-dimethylamino)-3-oxopropyl]thio]methyl]thio]-propanoic acid), alpha-naphthyl-beta-D-glucuronide, nitrobenzyl mercaptopurine riboside, probenecid, PSC833, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

The invention relates more preferably to the use of MRP4-inhibitors for preparing a pharmaceutical composition for treating respiratory complaints, containing the SYK-inhibitors and MRP4-inhibitors according to the invention, the MRP4-inhibitors preferably being selected from among dehydroepiandrosterone 3-sulphate, estradiol 3,17-disulphate, flurbiprofen, indomethacin, indoprofen, MK571, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the SYK-inhibitors, MRP4-inhibitors and another active substance according to the invention, such as, for example, an anticholinergic, a PDE4 inhibitor, a steroid, an LTD4-antagonist or a betamimetic, and the preparation thereof and the use thereof for treating respiratory complaints.

Compounds which may be used as iNOS inhibitors are compounds selected from among: S-(2-aminoethyl)isothiourea, aminoguanidine, 2-am inomethylpyridine, AMT, L-canavanine, 2-iminopiperidine, S-isopropylisothiourea, S-methylisothiourea, S-ethylisothiourea, S-methyltiocitrullin, S-ethylthiocitrulline, L-NA ($N^\omega$-nitro-L-arginine), L-NAME ($N^\omega$-nitro-L-argininemethylester), L-NMMA ($N^G$-monomethyl-L-arginine), L-NIO ($N^\omega$-iminoethyl-L-ornithine), L-NIL ($N^\omega$-iminoethyl-lysine), (S)-6-acetimidoylamino-2-amino-hexanoic acid (1H-tetrazol-5-yl)-amide (SC-51) (*J. Med. Chem.* 2002, 45, 1686-1689), 1400W, (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-trifluoromethyl-nicotinonitrile (WO 2004/041794), 2-((1R,3S)-3-amino-4-hydroxy-1-thiazol-5-yl-butylsulphanyl)-4-chloro-benzonitrile (WO 2004/041794), 2-((1R,3S)-3-amino-4-hydroxy-1-thiazol-5-yl-butylsulphanyl)-5-chloro-benzonitrile (WO 2004/041794), (2S,4R)-2-amino-4-(2-chloro-5-trifluoromethyl-phenylsulphanyl)-4-thiazol-5-yl-butan-1-ol (WO 2004/041794), 2-((1R,3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamine such as e.g. AR-C102222 (*J. Med. Chem.* 2003, 46, 913-916), (1S.5S.6R)-7-chloro-5-methyl-2-aza-bicyclo[4.1.0]hept-2-en-3-ylamine (ONO-1714) (*Biochem. Biophys. Res. Commun.* 2000, 270, 663-667), (4R, 5R)-5-ethyl-4-methyl-thiazolidin-2-ylideneamine (*Bioorg. Med. Chem.* 2004, 12, 4101), (4R,5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chloro-phenyl)-N-(1-{2-oxo-2-[4-(6-trifluoromethyl-pyrimidin-4-yloxy)-piperidin-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-ylmethyl-phenoxy)-ethoxy]-2-phenyl-pyridine (PPA250) (*J. Pharmacol. Exp. Ther.* 2002, 303, 52-57), methyl 3-{[(benzo[1,3]dioxol-5-yl-methyl)-carbamoyl]-methyl}-4-(2-imidazol-1-yl-pyrimidin-4-yl)-piperazine-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1,3]dioxol-5-yl-ethyl)-amide (BBS-2) (*Drugs Future* 2004, 29, 45-52) and the pharmaceutical salts, prodrugs or solvates thereof.

Examples of iNOS-inhibitors within the scope of the present invention may also include antisense oligonucleotides, particularly those antisense oligonucleotides which bind iNOS-coding nucleic acids. For example, WO 01/52902 describes antisense oligonucleotides, particularly antisense oligonucleotides, which bind iNOS coding nucleic acids, for modulating the expression of iNOS. iNOS-antisense oligonucleotides as described particularly in WO 01/52902 may therefore also be combined with the PDE4-inhibitors of the present invention on account of their similar effect to the iNOS-inhibitors.

8. FORMULATIONS

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance (s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain the compounds of formula 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, together with a naphthyridine according to formula 1 and one or more combination partners selected from those described above.

The invention claimed is:
1. A compound of formula 1 wherein
$R^1$ denotes a group A selected from among —O—$R^3$, —N$R^3R^4$, —C$R^3R^4R^5$, -(ethyne)-$R^3$, —S—$R^3$, —SO—$R^3$ and S$O_2$—$R^3$
or
$R^1$ denotes a group B selected from among
  $C_{6-10}$-aryl,
  five- to ten-membered, mono- or bicyclic heteroaryl with 1-3 heteroatoms selected independently of one another from among N, O and S; where this heteroaryl is linked to the structure according to formula 1 via either a C atom or an N atom,
  three- to ten-membered, mono- or bicyclic, saturated or partly saturated heterocyclic group with 1-3 heteroatoms selected independently of one another from among N, O and S, while this heterocyclic group is linked to the structure according to formula 1 via either a C atom or an N atom,
  and
  5- to 11-membered spiro group which may optionally contain 1, 2 or 3 heteroatoms selected independently of one another from among N, O and S, while this spiro group is linked to the structure according to formula 1 via either a C atom or an N atom,
while this group B may optionally be substituted by one or more groups selected independently of one another from among H, halogen, —$C_{1-3}$-alkyl, —NH($C_{1-4}$-alkyl), —N($C_{1-4}$-alkyl)$_2$, —NH$_2$, —$C_{1-3}$-alkyl-OH, —OH, oxo, —CO—NH$_2$, —$C_{1-3}$-alkylene-CO—NH$_2$, —CO—NH($C_{1-3}$-alkyl), —$C_{1-3}$-alkylene-CO—NH($C_{1-3}$-alkyl), —CO—NH($C_{3-5}$-cycloalkyl), —$C_{1-3}$-alkylene-CO—NH($C_{3-5}$-cycloalkyl), —NH—CO—NH$_2$, —NH—CO—NH($C_{1-3}$-alkyl), —NH—CO—N($C_{1-3}$-alkyl)$_2$, O—$C_{1-3}$-alkyl, —($C_{1-3}$-alkylene)-NH$_2$, -phenyl and —CO—($C_{1-5}$-alkyl),
$R^3$ is H
or a group selected from among —$C_{1-6}$-alkyl, —$C_{1-6}$-fluoroalkyl, —($C_{1-5}$-alkyl)-OH, —$C_{6-10}$-aryl, -($C_{1-4}$-alkylene)-($C_{6-10}$-aryl), -ethenyl, —($C_{1-4}$-alkylene)-(ethen), -ethynyl, —($C_{1-4}$-alkylene)-(ethyne), —($C_{1-4}$-alkylene)-(ethyne)-NH$_2$, —($C_{1-4}$-alkylene)-(ethyne)-($C_{1-4}$-alkylene)-NH$_2$, —NH($C_{1-3}$-alkyl), —($C_{1-4}$-alkylene)-NH($C_{1-3}$-alkyl), —CHOH—($C_{1-4}$-alkylene)-NH$_2$, —($C_{1-4}$-alkylene)-CHOH—($C_{1-4}$-alkylene)-NH$_2$, —($C_{1-4}$-alkylene)-CHOH—NH$_2$, —CHOH—NH$_2$, mono- or bicyclic, saturated or partly saturated —$C_{3-10}$-cycloalkyl, mono- or bicyclic, saturated or partly saturated —($C_{1-4}$-alkylene)-$C_{3-10}$-cycloalkyl, -(Het), —($C_{1-4}$-alkylene)-(Het), -(Hetaryl), and —($C_{1-4}$-alkylene)-(Hetaryl),
while this group
may optionally be substituted by one or more groups selected independently of one another from among H, —OH, -oxo, —COOH, -halogen, —$C_{1-3}$-alkyl, —$C_{1-3}$-haloalkyl, —$C_{1-3}$-alkyl-OH, —$C_{3-7}$-cycloalkyl, —O—($C_{1-4}$-alkyl), —NH($C_{1-4}$-alkyl), —($C_{1-4}$-alkylene)-NH($C_{1-4}$-alkyl), —N($C_{1-4}$-alkyl)$_2$, —($C_{1-4}$-alkylene)-N($C_{1-4}$-alkyl)$_2$, —NH—CO—NH$_2$, —($C_{1-4}$-alkylene)-NH—CO—NH$_2$, —CO—NH$_2$, —($C_{1-4}$-alkylene)-CO—NH$_2$, —CO—NH($C_{1-3}$-alkyl), —($C_{1-4}$-alkylene)-CO—NH($C_{1-3}$-alkyl), —CO—N($C_{1-3}$-alkyl)$_2$, —($C_{1-4}$-alkylene)-CO—N($C_{1-3}$-alkyl)$_2$, —NH—(CO)$_m$—NH$_2$, —NH—($C_{1-4}$-alkylene)-(CO)$_m$—NH$_2$, —NH—(CO)$_m$—NH($C_{1-3}$-alkyl), —NH—($C_{1-4}$-alkylene)-(CO)$_m$—NH($C_{1-3}$-alkyl), —NH—(CO)$_m$—N($C_{1-3}$-alkyl)$_2$, —NH—($C_{1-4}$-alkylene)-(CO)$_m$—N($C_{1-3}$-alkyl)$_2$, —O—($C_{2-4}$-alkylene)-NH$_2$, —O—($C_{2-4}$-alkylene)-NH($C_{1-3}$-alkyl), —O—($C_{2-4}$-alkylene)-N($C_{1-3}$-alkyl)$_2$, —NH—CO—($C_{1-3}$-alkyl), —($C_{1-4}$-alkylene)-NH—CO—($C_{1-3}$-alkyl), $C_{3-5}$-cycloalkyl, —S$O_2$—($C_{1-4}$-alkyl), —S$O_2$—($C_{3-5}$-cycloalkyl), —NH—S$O_2$—($C_{1-4}$-alkyl), —S$O_2$—NH$_2$, —S$O_2$—NH—$C_{1-3}$-alkyl, —S$O_2$—N($C_{1-3}$-alkyl)$_2$, —S$O_2$-(Het), —O-(Het), —O—($C_{1-4}$-alkylene)-(Het), —NH-(Het), —NH—($C_{1-4}$-alkylene)-(Het), —NH-(Hetaryl), —NH—($C_{1-4}$-alkylene)-(Hetaryl), -(Het) and —($C_{1-4}$-alkylene)-(Het),
wherein (Het) denotes a three- to ten-membered, saturated or partly saturated, mono- or bicyclic heterocyclic group, optionally substituted by 1-3 groups selected from $C_{1-3}$-alkyl, halogen, $CH_2$—NH$_2$, NH$_2$, OH, CO—NH$_2$ and oxo, which contains 1, 2 or 3 heteroatoms selected independently of one another from among N, O and S,
and
(Hetaryl) denotes a five- to ten-membered, mono- or bicyclic heteroaryl, optionally substituted by 1, 2 or 3 groups selected from $C_{1-3}$-alkyl, halogen, $CH_2$—NH$_2$, NH$_2$, OH, CO—NH$_2$ and oxo, which contains 1-3 heteroatoms selected independently of one another from among N, O and S,
m=0 or 1
$R^4$ and $R^5$ denote H, methyl or ethyl
$R^6$ denotes methyl, as well as pharmaceutically acceptable salts thereof.
2. The compound of formula 1 according to claim 1, wherein
$R^6$ is methyl,
as well as pharmaceutically acceptable salts thereof.
3. The compound of formula 1 according to claim 1, wherein
$R^1$ is —O—$R^3$ or —N$R^3R^4$,
as well as pharmaceutically acceptable salts thereof.
4. The compound of formula 1 according to claim 3, wherein $R^1$ is —O—$R^3$ or —N$R^3R^4$
and
(Het) denotes a three- to seven-membered, saturated or partly saturated, monocyclic heterocyclic group, optionally substituted by 1-3 groups selected from methyl, ethyl propyl, isopropyl, F, Cl, Br, $CH_2$—NH$_2$, NH$_2$, OH, CO—NH$_2$ and oxo, which contains 1, 2 or 3 heteroatoms selected independently of one another from among N, O and S, and
(Hetaryl) denotes a five- to six-membered, monocyclic heteroaryl, optionally substituted by 1, 2 or 3 groups selected from methyl, ethyl propyl, isopropyl, F, Cl, Br, $CH_2$—NH$_2$, NH$_2$, OH, CO—NH$_2$ and oxo, which contains 1-3 heteroatoms selected independently of one another from among N, O and S, as well as pharmaceutically acceptable salts thereof.

5. The compound of formula 1 according to claim 1, wherein $R^1$ is selected from among five- to ten-membered, mono- or bicyclic heteroaryl with 1-3 heteroatoms selected independently of one another from among N, O and S; where at least one of the 1-3 heteroatoms is an N atom and three- to ten-membered, mono- or bicyclic, saturated or partly saturated heterocyclic group with 1-3 heteroatoms selected independently of one another from among N, O and S, where at least one of the 1-3 heteroatoms is an N atom, wherein the above-mentioned heteroaryls and heterocycles are each linked to the structure according to formula 1 by means of the at least one N atom, or wherein $R^1$ is a 5- to 11-membered spiro group which contains 1, 2 or 3 heteroatoms selected independently of one another from among N, O and S, where at least of one of the 1-3 heteroatoms of this spiro group is an N atom and the spiro group is linked to the structure according to formula 1 via this N atom, as well as pharmaceutically acceptable salts thereof.

6. The compound of formula 1 according to claim 1, wherein $R^1$ is selected from among

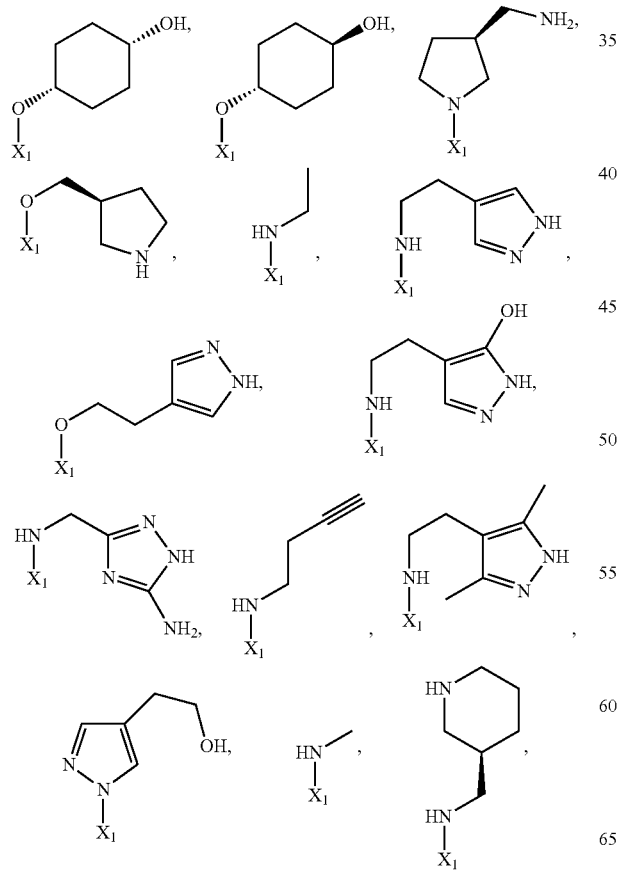

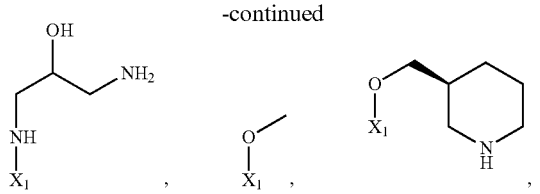

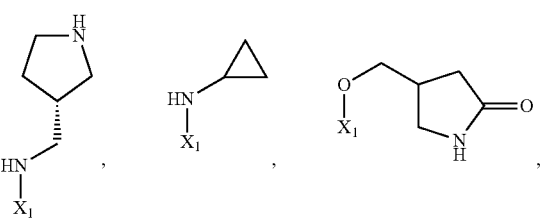

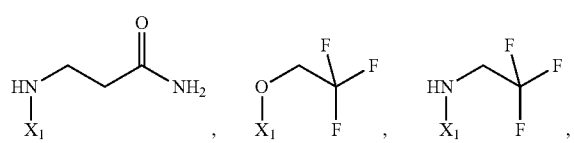

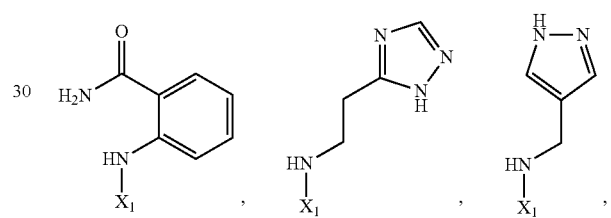

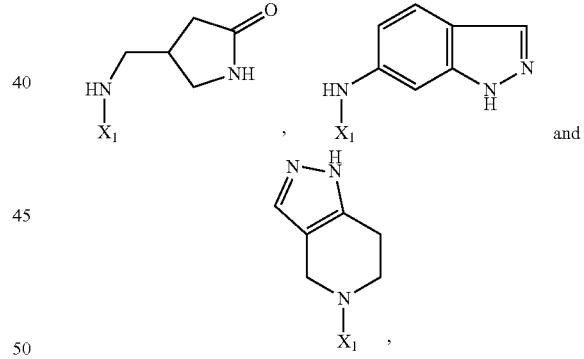

where $X_1$ denotes the point of attachment of $R^1$ to the structure of formula 1 and wherein $R^6$ is methyl, as well as pharmaceutically acceptable salts thereof.

7. A pharmaceutical composition comprising one or more compounds of formula 1 according to claim 1 or pharmaceutically acceptable salts thereof and pharmaceutically acceptable excipients and/or carriers.

8. A pharmaceutical composition comprising one or more compounds of formula 1 according to claim 1 or pharmaceutically acceptable salts thereof and pharmaceutically acceptable excipients and/or carriers in combination with an active substance selected from among betamimetics, corticosteroids, PDE4-inhibitors, EGFR-inhibitors and LTD4-antagonists, CCR3-inhibitors, iNOS-inhibitors and SYK-inhibitors.

9. A compound selected from
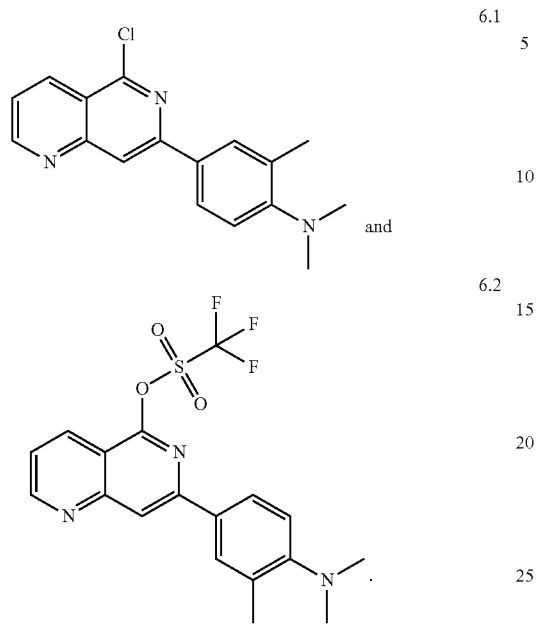
6.1
and
6.2
* * * * *

UNITED STATES PATENT AND TRADEMARK OFFICE
CERTIFICATE OF CORRECTION

PATENT NO.        : 8,604,049 B2
APPLICATION NO.   : 13/057330
DATED             : December 10, 2013
INVENTOR(S)       : Fiegen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 335 days.

Signed and Sealed this
Twenty-third Day of May, 2017

Michelle K. Lee
*Director of the United States Patent and Trademark Office*